United States Patent
Ho

(10) Patent No.: US 8,263,151 B2
(45) Date of Patent: Sep. 11, 2012

(54) PERACID AND 2-HYDROXY ORGANIC ACID COMPOSITIONS AND METHODS FOR TREATING PRODUCE

(75) Inventor: Kai Lai Grace Ho, Salinas, CA (US)

(73) Assignee: Fresh Express, Incorporated, Salinas, CA (US)

( * ) Notice: Subject to any disclaimer, the term of this patent is extended or adjusted under 35 U.S.C. 154(b) by 376 days.

(21) Appl. No.: 12/491,155

(22) Filed: Jun. 24, 2009

(65) Prior Publication Data

US 2009/0324789 A1    Dec. 31, 2009

Related U.S. Application Data

(60) Provisional application No. 61/075,267, filed on Jun. 24, 2008.

(51) Int. Cl.
*A23L 3/3463* (2006.01)

(52) U.S. Cl. .................. 426/335; 426/321; 424/616

(58) Field of Classification Search .................. 426/335
See application file for complete search history.

(56) References Cited

U.S. PATENT DOCUMENTS

| | | | |
|---|---|---|---|
| 2,512,640 A | 6/1950 | Greenspan et al. | |
| 4,311,598 A | 1/1982 | Verachtert | |
| 5,168,655 A | 12/1992 | Davidson et al. | |
| 5,200,189 A | 4/1993 | Oakes et al. | |
| 5,409,713 A | 4/1995 | Lokkesmoe et al. | |
| 5,565,231 A | 10/1996 | Malone et al. | |
| 5,632,676 A | 5/1997 | Kurschner et al. | |
| 5,656,231 A | 8/1997 | Blackmore | |
| 5,674,538 A | 10/1997 | Lokkesmoe et al. | |
| 5,683,724 A | 11/1997 | Hei et al. | |
| 5,718,910 A | 2/1998 | Oakes et al. | |
| 6,113,963 A | 9/2000 | Gutzmann et al. | |
| 6,183,807 B1 * | 2/2001 | Gutzmann et al. | 426/652 |
| 6,319,888 B2 | 11/2001 | Wei et al. | |
| 6,455,086 B1 * | 9/2002 | Trinh et al. | 426/321 |
| 6,475,967 B1 | 11/2002 | Arvanitidou et al. | |
| 6,506,417 B1 | 1/2003 | Siddle | |
| 6,545,047 B2 | 4/2003 | Gutzmann et al. | |
| 6,593,283 B2 | 7/2003 | Hei et al. | |

(Continued)

FOREIGN PATENT DOCUMENTS

EP    0233731 A2    8/1987

(Continued)

OTHER PUBLICATIONS

Martínez-Sánchez: Microbial, nutritional and sensory quality of rocket leaves as affected by different sanitizers; Postharvest Biology and Technology: vol. 42, Issue 1, Oct. 2006, pp. 86-97.*

(Continued)

*Primary Examiner* — Humera Sheikh
*Assistant Examiner* — Patricia George
(74) *Attorney, Agent, or Firm* — Kilpatrick Townsend & Stockton LLP

(57) ABSTRACT

Methods and compositions for treating produce to control microorganisms are provided. The method treats produce by contacting the surface of the produce with an aqueous solution comprising i) an organic peracid of the formula RC(O)OOH wherein R is methyl, ethyl, n-propyl, or s-propyl; ii) a 2-hydroxy organic acid selected from tartaric acid, citric acid, malic acid, mandelic acid, and lactic acid; and (optionally) iii) an anionic surfactant; wherein the aqueous solution has a pH from 2.5 to 6.0.

15 Claims, 16 Drawing Sheets

Flume-Water Suspended-Cells Challenge Tests

FE has the highest log reductions on *E. coli K12* and *Listeria innocua* suspended in flume water

U.S. PATENT DOCUMENTS

| | | | |
|---|---|---|---|
| 6,627,657 | B1 | 9/2003 | Hilgren et al. |
| 6,635,286 | B2 | 10/2003 | Hei et al. |
| 6,767,569 | B1 | 7/2004 | Marsden et al. |
| 6,828,294 | B2 | 12/2004 | Kellar et al. |
| 6,927,237 | B2 | 8/2005 | Hei et al. |
| 7,148,187 | B1 | 12/2006 | Simon et al. |
| 7,150,884 | B1 * | 12/2006 | Hilgren et al. ............... 424/616 |
| 7,381,439 | B2 | 6/2008 | Hilgren et al. |
| 2004/0143133 | A1 | 7/2004 | Smith et al. |
| 2005/0163896 | A1 | 7/2005 | Man et al. |
| 2007/0166441 | A1 | 7/2007 | Adams et al. |
| 2007/0258915 | A1 | 11/2007 | Kielbania |
| 2007/0297942 | A1 | 12/2007 | Samadpour |
| 2009/0117206 | A1 | 5/2009 | Carpenter et al. |
| 2009/0291173 | A1 | 11/2009 | Harvey et al. |
| 2009/0312226 | A1 | 12/2009 | Szewczyk et al. |
| 2009/0324789 | A1 | 12/2009 | Ho |
| 2010/0003341 | A1 | 1/2010 | Besendorfer |
| 2010/0234328 | A1 | 9/2010 | Ahmed et al. |
| 2010/0240765 | A1 | 9/2010 | Lange et al. |

FOREIGN PATENT DOCUMENTS

| | | |
|---|---|---|
| EP | 0456627 A2 | 11/1991 |
| EP | 0569066 A1 | 11/1993 |
| EP | 0460962 B1 | 12/1995 |
| EP | 0720814 A1 | 7/1996 |
| EP | 0 971 584 B1 | 1/2003 |
| EP | 1 248 601 B1 | 9/2003 |
| GB | 2152377 A | 8/1985 |
| GB | 2207354 A | 2/1989 |
| WO | WO 93/02973 | 2/1993 |
| WO | WO 2004/108171 A1 | 12/2004 |
| WO | WO 2008/031087 A1 | 3/2008 |
| WO | WO 2008/031104 A2 | 3/2008 |
| WO | WO 2008/079999 A1 | 7/2008 |
| WO | WO 2009/027857 A1 | 3/2009 |

OTHER PUBLICATIONS

21 CFR §178.1010—Sanitizing solutions. Food and Drugs (Dec. 2005).

Brown, G. Eldon, "Effect of Experimental Bacterial Disinfectants Applied to Oranges on Postharvest Decay," *Proc. Fla. State Hort. Soc.* 100:20-22 (1987).

Greenspan, Frank P. et al., "The Application of Peracetic Acid Germicidal Washes to Mold Control of Tomatoes," *Food Technology, The Institute of Food Technologies*, 5(3):95-97 (Mar. 1951).

International Search Report mailed on Sep. 6, 2010, for PCT Application No. PCT/US2009/048517 filed on Jun. 24, 2009, 14 pages.

Iverson, Claire et al., "Developments in Beet and Cane Sugar Extraction," *Food Technology* 38:40-44 (Jan. 1984).

Nystrand, Rolf, "Disinfectants in Beet Sugar Extraction," *Zuckerind.* 110(8):693-698 (1985).

Rupasinghe, H. P. Vasantha et al., "Lactic acid improves the efficacy of anti-microbial washing solutions for apples," *Journal of Food, Agriculture & Environment* 4(2):44-48 (2006).

Sagong, Hun-Gu et al., "Combined effect of ultrasound and organic acids to reduce *Escherichia coli* O157:H7, *Salmonella* Typhimurium, and *Listeria monocytogenes* on organic fresh lettuce," Intl. J. of Food Microbiology, 2011, vol. 145, pp. 287-292.

Torriani, S. et al., "Potential of *Lactobaccillus casei*, culture permeate, and lactic acid to control microorganisms in ready-to-use vegetables," J. Food Protec, 1997, vol. 60, No. 12, pp. 1564-1567.

Uyttendaele, M. et al., "Control of *Aeromonas* on minimally processed vegetables by decontamination with lactic acid, chlorinated water, or thyme essential oil solution," International Journal of Food Microbiology, 2004, vol. 90, pp. 263-271.

Vandekinderen, I. et al., "Optimization and evaluation of decontamination step with peroxyacetic acid for fresh-cut produce," Food Microbiology, 2009, vol. 26, pp. 882-888.

Venkitanarayanan K.S. et al., "Inactivation of *Escherichia coli* O157:H7 and *Listeria monocytogenes* on apples, oranges, and tomatoes by lactic acid with hydrogen peroxide," J. Food Protec, 1999, vol. 67, No. 6, pp. 1238-1242.

Yuk, Hyun-Gyun et al., "Effect of combined ozone and organic acid treatment for control of *Escherichia coli* O157:H7 and *Listeria monocytogenes* on lettuce," Journal of Food Science, 2006, vol. 71, No. 3, pp. M83-M87.

Zhang, G. et al., "Efficacy of antimicrobial agents in lettuce leaf processing water control of *Escherichia coli* O157:H7," J. of Food Protection, 2009, vol. 72, No. 7, pp. 1392-1397.

Akbas, M.Y. et al., "Effectiveness of organic acid, ozonated water and chlorine dippings on microbial reduction and storage quality of fresh-cut iceberg lettuce," J. Sci Food Agric, 2007, vol. 87, pp. 2609-2616.

Akbas, M.Y. et al., "Inactivation of *Escherichia coli* and *Listeria monocytogenes* on iceberg lettuce by dip wash treatments with organic acids," The Society for Applied Microbiology, Letters in Applied Microbiology, 2007, vol. 44, pp. 619-624.

Beuchat, L.R. et al., "Efficacy of chlorine and a peroxyacetic acid sanitizer in killing *Listeria monocytogenes* on iceberg and romaine lettuce using simulated commercial processing conditions," J. Food Protec, 2004, vol. 67, No. 6, pp. 1238-1242.

Castaner, M. et al., Organic acids as browning inhibitors on harvested "baby" lettuce and endive, Z Lebensm Unters Forsch A, 1997, vol. 205, pp. 375-379.

Escudero M.E. et al., "Effectiveness of various disinfectants in the elimination of *Yersinia enterocolitica* on fresh lettuce," Journal of Food Protection, 1999, vol. 62, No. 6, pp. 665-669.

Huang, Y. et al., "Effect of organic acids, hydrogen peroxide and mild heat on inactivation of *Escherichia coli* O157:H7 on baby spinach," Food Control, 2011, vol. 22, pp. 1178-1183.

McWatters, K.H. et al., "Acceptability of Lettuce treated with a lactic acid and hydrogen peroxide antibacterial solution," J. of Food Quality, 2002, vol. 25, pp. 223-242.

McWatters, K.H. et al., "Consumer acceptance of fresh-cut iceberg lettuce treated with 2% hydrogen peroxide and mild heat," J. of Food Protection, 2002, vol. 65, No. 8, pp. 1221-1226.

Parish, M.E. et al., "Methods to reduce/eliminate pathogens from fresh and fresh-cut produce," Comprehensive Reviews in Food Science and Food Safety, 2003, vol. 2 (supplement), pp. 161-173.

Park, Sang-Hyun et al., "Use of organic acids to inactivate *Escherichia coli* O157:H7, *Salmonella* Typhimurium, and *Listeria monocytogenes* on organic fresh apples and lettuce," Journal of Food Science, 2011, vol. 76, No. 6, pp. M293-M298.

Rodgers, S.L. et al., "Comparison of different chemical sanitizers for inactivating *Escherichia coli* O157:H7 and *Listeria monocytogenes* in solution and on apples, lettuce, strawberries, and cantaloupe," J. Food Protec, 2004, vol. 67, No. 4, pp. 721-731.

Adams, M.R. et al, "Factors affecting the efficacy of washing procedures used in the production of prepared salads," Food Microbiology, 1989, vol. 6, pp. 69-77.

Allende, Ana et al., "Role of commercial sanitizers and washing systems on epiphytic microorganisms and sensory quality of fresh-cut escarole and lettuce," *Postharvest Biology and Technology* (2008) 49:155-163.

Guan, Wenqiang et al., "Acids in Combination with Sodium Dodecyl Sulfate Caused Quality Deterioration of Fresh-Cut Iceberg Lettuce during Storage in Modified Atmosphere Package," *Journal of Food Science* (2010) 00(0):S1-S6.

Ho, Kai-Lai Grace et al., "Efficacy of a Novel Sanitizer Composed of Lactic Acid and Peroxyacetic Acid against Single Strains of Nonpathogenic *Escherichia coli* K-12, *Listeria innocua*, and *Lactobacillus plantarum* in Aqueous Solution and on Surfaces of Romaine Lettuce and Spinach," *Journal of Food Protection* (2011) 74(9):1468-1474.

Lin, Chia-Min et al., "Inactivation of *Escherichia coli* O157:H7, *Salmonella enterica* Serotype enteritidis, and *Listeria monocytogenes* on Lettuce by Hydrogen Peroxide and Lactic Acid and by Hydrogen Peroxide with Mild Heat," *Journal of Food Protection* (2002) 65(8):1215-1220.

Martinez-Sanchez, Ascension et al., "Microbial, nutritional and sensory quality of rocket leaves as affected by different sanitizers," *Postharvest Biology and Technology* (2006) 42:86-97.

Olmez, Hulya et al., "Potential alternative disinfection methods for organic fresh-cut industry for minimizing water consumption and environment impact," *LWT—Food Science and Technology* (2009) 42:686-693.

Velazquez, Lidia del Carmen et al., "Evaluation of chlorine, benzalkonium chloride and lactic acid as sanitizers for reducing *Escherichia coli* O157:H7 and *Yersinia enterocolitica* on fresh vegetables," *Food Control* (2009) 20:262-268.

Venkitanarayanan, Kumar S. et al., "Inactivation of *Escherichia coli* O157:H7, *Salmonella enteritidis*, and *Listeria monocytogenes* on Apples, Oranges, and Tomatoes by Lactic Acid with Hydrogen Peroxide," *Journal of Food Protection* (2002) 65(1):100-105.

Zhang, S. et al., "The effects of various disinfectants against *Listeria monocytogenes* on fresh-cut vegetables," *Food Microbiology* (1996) 13:311-321.

21 CFR Subpart A General Provisions, Section 184.1 *Substances added directly to human food affirmed as generally recognized as safe (GRAS)* (Oct. 1997); Electronic Code of Federal Regulations (e-CFR Data is current as of Dec. 13, 2011); pp. 1-6.

21 CFR Subpart B Listing of Specific Substances Affirmed as GRAS, Section 184.1005 *Acetic acid* (Jun. 1982); Electronic Code of Federal Regulations (e-CFR Data is current as of Dec. 13, 2011); pp. 6-7.

21 CFR Subpart B Listing of Specific Substances Affirmed as GRAS, Section 184.1033 *Citric acid* (Dec. 1994), Electronic Code of Federal Regulations (e-CFR Data is current as of Dec. 13, 2011); pp. 11-12.

21 CFR Subpart B Listing of Specific Substances Affirmed as GRAS, Section 184.1061 *Lactic acid* (Sep. 1984), Electronic Code of Federal Regulations (e-CFR Data is current as of Dec. 13, 2011); pp. 12-13.

* cited by examiner

Effects of FE on Quality and Shelf Life of Spring Mix w/ low moisture content

Significant Reduction in Off-Odor

Off-Odor Scores on Day 11 of the FE samples is 67% less than that of the Chlorinated Water samples

Effects of FE on Quality and Shelf Life of Spring Mix w/ low moisture content

Inhibited Spoilage Microorganisms

Day 8 FE spoilage microbial load is equivalent to the 1st day of Chlorinated water

Effects of FE on Quality and Shelf Life of Spring Mix w/ high moisture content

Enhanced Microbial Reduction

Log Reduction on indigenous microorganisms by FE is 2.3 to 6 folds better than Chlorinated water

Effects of FE on Quality and Shelf Life of Spring Mix w/ high moisture content

Inhibited Growth of Indigenous Microorganisms

Day 8 FE indigenous microbial load is equivalent to the 4th day of Chlorinated water

Effects of FE on Quality and Shelf Life of Spinach

Significant Reduction in Decay

Decay on Day 13 of the FE samples was 47% less than that of the Chlorinated Water samples

Effects of FE on Quality and Shelf Life of Spinach

Significant Reduction in Off-Odor

Off-Odor Scores on Day 13 of FE is 42% less than that of Chlorinated Water

Effects of FE on Quality and Shelf Life of Spinach
Inhibited Spoilage Microorganisms Day 9 FE spoilage microbial load is equivalent to the 1st day of Chlorinated water
Day 15 FE spoilage microbial load is equivalent to the 9th day of Chlorinated water

PERACID AND 2-HYDROXY ORGANIC ACID COMPOSITIONS AND METHODS FOR TREATING PRODUCE

CROSS-REFERENCES TO RELATED APPLICATIONS

This application claims priority benefit of U.S. Provisional Application Ser. No. 61/075,267, filed on Jun. 24, 2008, the contents of which are incorporated in their entirety for all purposes.

STATEMENT AS TO RIGHTS TO INVENTIONS MADE UNDER FEDERALLY SPONSORED RESEARCH AND DEVELOPMENT

Not applicable

REFERENCE TO A "SEQUENCE LISTING," A TABLE, OR A COMPUTER PROGRAM LISTING APPENDIX SUBMITTED ON A COMPACT DISK.

Not applicable

BACKGROUND OF THE INVENTION

Safe and reliable means of removing microorganisms from the surface of produce such as fruits and vegetables is of growing public health concern given the increased growth in their international trade and consumption. Existing methods for removing or reducing microorganisms from food do not adequately control microorganisms that have the potential to cause disease or spoil the produce. Accordingly, there is a large need for new methods and compositions that can greatly reduce the presence of microorganisms on produce.

This invention provides compositions and methods that meet these needs.

BRIEF SUMMARY OF THE INVENTION

The invention provides compositions and methods useful in sanitizing and maintaining the quality of produce, for example, fruits and vegetables. In a first aspect, the invention provides compositions useful in sanitizing produce. The compositions are aqueous solutions having a pH of 2.5 to 6.0 and comprising i) an organic peracid of the formula RC(O)OOH wherein R is methyl, ethyl, n-propyl, or s-propyl; ii) a 2-hydroxy organic acid selected from tartaric acid, citric acid, malic acid, mandelic acid, and lactic acid; iii) water; and optionally iv), an anionic surfactant. In preferred embodiments, the peracid is peroxyacetic acid (also known as peracetic acid or acetyl hydroperoxide), the organic acid is lactic acid (also known as 2-hydroxypropionic acid), and if present, the preferred anionic surfactant is sodium lauryl sulfate. Because aqueous sanitizing solutions of peracids may exist in equilibrium with, or be formed from concentrated solutions of, hydrogen peroxide, their corresponding acid, and water, the aqueous sanitizing solutions may also contain hydrogen peroxide and the corresponding acid (e.g., acetic acid in the case of peroxyacetic acid). The sanitizing solutions may be provided as concentrates or in ready-to-use aqueous formulations. The compositions may also be provided as part of a kit for use in sanitizing or treating produce.

In a second aspect the invention provides methods of sanitizing or treating produce, including vegetables and fruits by contacting the surface of the produce with an aqueous sanitizer solution of the invention. The contacting can sanitize the surface of the produce by greatly reducing the number of microbes, including any human pathogens, present or adhering to the surface of the produce. The contacting can also serve to prevent spoilage of the produce due to indigenous microbial contamination on the surface of the produce. The contacting can also serve to preserve the quality of the produce during storage by reducing off-odors, decay, and/or inhibiting the growth of indigenous microbes on the surface of the produce.

DETAILED DESCRIPTION OF THE INVENTION

Figure 1:
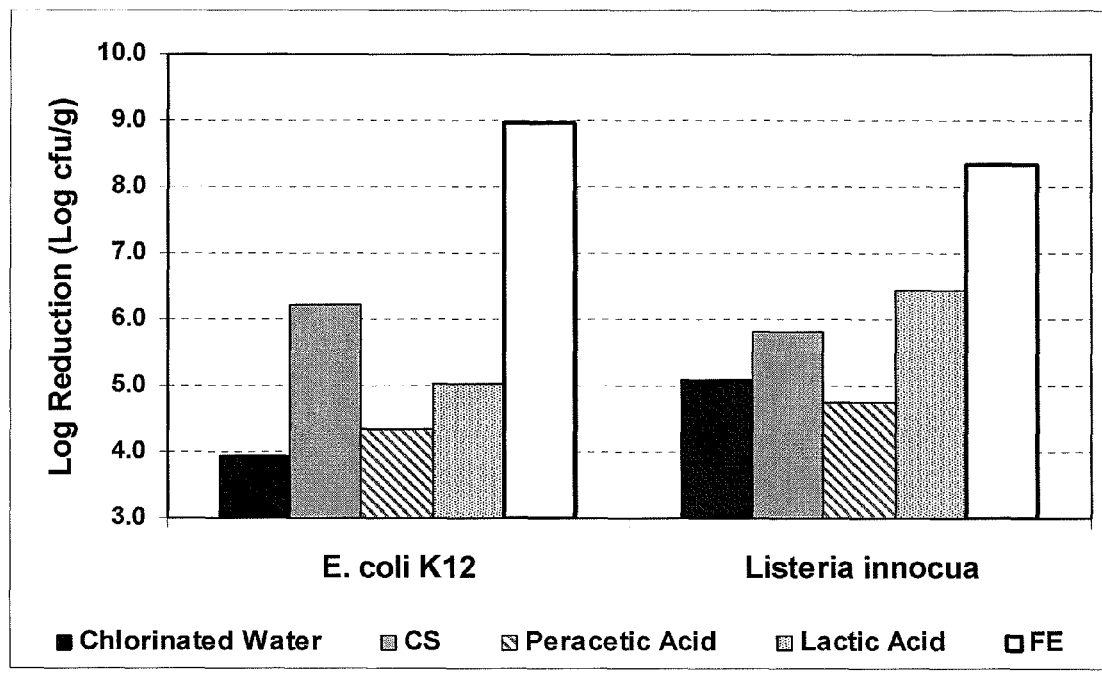
FIG. 1 is a comparison of five treatments, in left to right order: a) chlorinated water: 50-70 ppm active chlorine at pH 6.5; b) CS: a commercial antimicrobial produce cleaner with major active ingredients as citric acid plus surfactants; c) Peroxyacetic acid: 70 to 80 ppm peroxyacetic acid+0.01% surfactant; d) lactic acid solution: 0.9 to 1.2% lactic acid+0.01% surfactant; and e) FE: 70 to 80 ppm peroxyacetic acid+0.9 to 1.2% lactic acid+0.01% surfactant) on flume-water suspended cells challenge test. The surfactant used was sodium lauryl sulfate.

The invention relates to the discovery that an aqueous solution comprising peroxyacetic acid, lactic acid, and (optionally) sodium lauryl sulfate is surprisingly effective in treating produce to reduce microbial contamination on the surface of treated produce and to prevent spoilage or decay of the treated produce. These advantages have been shown for lettuce, spinach and a spring mix of various baby lettuces and greens. The combination of the ingredients is much more effective at reducing leaf-attached microbes than any one of the ingredients acting alone and is also especially efficacious in reducing the decay or spoilage of produce.

Peroxyacetic acid antimicrobial activity relies on its high oxidizing potential. The mechanism of oxidation is the transfer of electrons, therefore the stronger the oxidizer, the faster the electrons are being transferred to the microorganism and the faster the microorganism is inactivated or killed. Therefore based on the table below peroxyacetic acid has a higher oxidation potential than chlorine sanitizers but less than that of ozone.

| Oxidation Capacity of Selected Sanitizers | |
|---|---|
| Sanitizer | eV* |
| Ozone | 2.07 |
| Peroxyacetic acid | 1.81 |
| Chlorine Dioxide | 1.57 |
| Sodium hypochlorite (Chlorine bleach) | 1.36 |

*electron-Volts

As diffusion of the molecule is slower than its half-life, peroxyacetic will react with any oxidizable compounds in its vicinity. It can damage virtually all types of macromolecules associated with a microorganism; for e.g. carbohydrates, nucleic acids (mutations), lipids (lipid peroxidation) and amino acids (e.g. conversion of Phe to m-Tyr and o-Tyr), and ultimately lysis the cell. Conventionally 2-hydroxy organic acids such as lactic acid that possess the chemical properties of oxidizable organic compounds would be taught away from being used together with a strong oxidizer, particularly with reference to peracids. Hence, it is particularly surprising to combine the peracetic acid and lactic acid in this invention and shown that the two compounds have synergistic effects rather than one counteracting against the other.

Definitions

It must be noted that, as used in this specification and the appended claims, the singular forms "a," "an" and "the" include plural referents unless the content clearly dictates otherwise. Thus, for example, reference to a "surfactant" includes two or more such surfactants.

Unless defined otherwise, all technical and scientific terms used herein have the same meaning as commonly understood by one of ordinary skill in the art to which the invention pertains. All ranges are inclusive of the end values.

With reference to the aqueous solutions and methods of the invention, "peracid" and "organic peracid" refer to compounds of the structure RC(O)OOH in which R is an aliphatic group having from 1 to 3 carbon atoms. R may be methyl, ethyl, n-propyl, or s-propyl. A particularly preferred peracid is peracetic acid/peroxyacetic acid/PAA/(CH₃C(O)OOH). Mixtures of the above organic peracids may be used.

In aqueous solutions, organic peracids exist in a chemical equilibrium with hydrogen peroxide and accordingly can be formed from the corresponding organic acids and hydrogen peroxide in the reaction:

The equilibrium concentration of each reactant can be calculated from the equilibrium equation:

$$([RCOOOH][H_2O])/([RCOOH][H_2O_2])=K_{ap} \quad \text{(Eq. 1)}$$

wherein: [RCOOOH] is the concentration of peracid in mole/L; [H₂O] is the concentration of water in mole/L; [RCOOH] is the concentration of organic acid in mole/L; and [H₂O₂] is the concentration of hydrogen peroxide in mole/L; and $K_{ap}$ is the apparent equilibrium constant for the peracid equilibrium reaction (Equation 1).

The apparent equilibrium constant, $K_{ap}$, varies with both the peracid chosen and with temperature. Equilibrium constants for peracid formation can be found in D. Swem, ed., Organic Peroxides, Vol. 1, Wiley-Interscience, New York, 1970. At a temperature of 40° C., the apparent equilibrium constant for peroxyacetic acid is about 2.21. In accordance with this equilibrium reaction, organic peracid solutions comprise hydrogen peroxide and the corresponding organic acid in addition to the organic peracid.

When diluted, a relatively long period of time may lapse before a new equilibrium is achieved. For instance, equilibrium solutions that comprise about 5% peroxyacetic acid typically comprise about 22% hydrogen peroxide. Equilibrium solutions that comprise about 15% peroxyacetic acid typically comprise about 10% hydrogen peroxide. When these equilibrium solutions are diluted to solutions that comprise about 50 ppm of peroxyacetic acid, the solution produced by dilution of the 5% peroxyacetic acid solution comprises about 220 ppm of hydrogen peroxide, and the solution produced by dilution of 15% solution comprises about 33 ppm of hydrogen peroxide. Accordingly, in some embodiments, the sanitizing solution is provided as a concentrate which is diluted to the desired peracid concentration with water or with an aqueous solution comprising other components of the sanitizing solution according to the invention just prior to use. In some embodiments, the sanitizing solutions are provided as concentrates which are diluted just prior to use.

Peracids are readily commercially available in accordance with the above equilibrium. Peroxyacetic acid (CAS No. 79-21-0) is readily commercially available, for instance, as aqueous solution comprising peroxyacetic acid (35%), hydrogen peroxide (6.5%), acetic acid 64-19-7 (40%), sulfuric acid (about 1%) and water (about 17%) (all units w/w).

The 2-hydroxy organic acid is selected from tartaric acid, citric acid, malic acid, mandelic acid, and lactic acid. The predominant biological optical isomers are preferred. The 2-hydroxy organic acid can also be provided as the racemate, as well as any of its optically pure isomers. In some embodiments, the (+) enantiomer is preferred (e.g., L-lactic acid, L(+)-Lactic acid).

As used herein, the term "sanitize" shall mean the reduction of viable microorganisms on surfaces with the exception of bacterial endospores. In some embodiments, the reduction is by at least 99.9%, 99.99%, 99.999% (e.g., by 3, 4, or 5 log units, respectively) or at least by 3, 4, 5, 6, 7, 8, or log units as measured before and after contact with the sanitizing solutions according to the invention. In some embodiments, the sanitized surfaces have levels of pathogenic microorganisms considered safe according to any applicable public health ordinance or below thresholds thought to pose risk of infection or disease. Accordingly, a surface need not have complete elimination or destruction of all forms of microbial life to be sanitized. The reduction may be by physical removal, or toxicity to the microorganism leading to the destruction or inhibition of the growth of the microorganism.

"Produce" references whole or cut organic and non-organic vegetables and fruits, including but not limited to those which are eaten uncooked. In some embodiments, the produce is Spring Mix, spinach, Romaine lettuce, avocado, yam, asparagus, escarole, arugula, radicchio, pea shoots, dill, chives, head lettuce, leaf lettuce (e.g., red and green lettuce), Iceberg lettuce, endive, parsley, spinach, radishes, celery, carrots, beets, onions, rhubarb, eggplant, peppers, pumpkins, zucchini, cucumbers, tomatoes, potatoes, sweet potatoes, turnips, rutabagas, zucchini, cabbage (e.g., red and green cabbage), kale (e.g., green and purple kale), kohlrabi, collard greens, cauliflower, oriental vegetables (e.g., baby bakchoy, string beans, mustard plant, Chinese broccoli, napa cabbage, chives, cilantro, yau-choy, loofah), Brussels sprouts, okra, mushrooms, snow pea, soybean, broccoli, snapdragon pea, corn, and dandelion greens; fruits such as apples, pineapple, melons (e.g., cantaloupe, watermelon, honeydew, muskmelon, winter melon), citrus fruit (e.g., orange, lemon, tangerine, grapefruit), golgi, acai, peaches, cherries, apricots, persimmons, kiwi, quince, plums, prunes, grapes, and pears; and berries such as strawberries, raspberries, gooseberries, loganberries, boysenberries, cranberries, currants, elderberries, blackberries, and blueberries.

The term "essentially free" means that the referenced compound or substance is present in the solution at a level less than about 300, preferably less than about 150 and more preferably less than about 50 and most preferably less than about 10 ppm or even 1 ppm by weight.

Compositions of the Invention

Accordingly, in a first aspect, the invention provides an aqueous solution comprising 1) an organic peracid of the formula RC(O)OOH wherein R is methyl, ethyl, n-propyl, or s-propyl; ii) a 2-hydroxy organic acid selected from tartaric acid, citric acid, malic acid, mandelic acid, and lactic acid; iii) water; and optionally, iv) an anionic surfactant, wherein the aqueous solution has a pH from 2.5 to 6.0. In some embodiments, the pH is from 2.5 to 3.5, 2.5 to 4.0, 2.7 to 3.5, 2.5 to 5.0, 3.0 to 4.0, 3.0 to 5.0, 3.0 to 6.0, or from 3.5 to 4.5.

Suitable 2-hydroxy organic acids for use in the aqueous solutions of the invention are tartaric acid, citric acid, malic acid, mandelic acid, and lactic acid (i.e., 2-hydroxypropanoic acid). An exemplary 2-hydroxy organic acid is lactic acid. A combination of two or more of any of the above 2-hydroxy organic acids may be used (e.g., lactic acid+citric acid; lactic acid+tartaric acid; lactic acid+malic acid; lactic acid+mandelic acid).

In some embodiments, the peracid is peroxyacetic acid, the organic acid is lactic acid, and the anionic surfactant is sodium lauryl sulfate. In other embodiments, the concentration of peracid acid in the solution is from 3 to 100 ppm (w/w), the concentration of 2-hydroxy organic acid in the solution is from 0.1% to 2% (w/w); and the pH is between 2.5 and 5.0. In a still further embodiment, the concentration of peracid is 5 to 100 ppm (w/w), the concentration of 2-hydroxy organic acid is 0.1 to 2% (w/w).

In an additional embodiment, the aqueous solution of the invention, has a concentration of peracid in the solution from about 60 to 80 ppm (w/w), a concentration of 2-hydroxy organic acid in the solution of from about 0.2% to 1.25% (w/w); and a pH between about 2.8 to 4.2 or 3.8 and 4.2, inclusive.

In some embodiments, the concentration of the peracid in the solution can be from 3 to 100 ppm (w/w), the concentration of 2-hydroxy organic acid in the solution from 0.1% to 2% (w/w); and the pH is between 2.5 and 5.0. In a still further embodiment, the concentration of peracid is 50 to 100 ppm (w/w) and the concentration of 2-hydroxy organic acid is 0.1 to 1% (w/w). In further embodiments, the peracid is peroxyacetic acid and the 2-hydroxy organic acid is lactic acid (e.g., L(+)-lactic acid). In still further embodiments, the concentration of the peracetic acid is 60 to 90 ppm or 70 to 80 ppm. In still further embodiments of such, the concentration of the lactic acid is 0.1 to 0.8% or 0.2 to 0.4% (w/w).

In a particularly preferred embodiment, the invention provides a composition comprising, or consisting essentially of, an aqueous solution of peroxyacetic acid and lactic acid (e.g., L-(+)-Lactic acid) at a pH of from about 2.5 to 6.0, and more preferably at a pH between 2.8 to 4.2 or 3.8 to 4.2, inclusive, wherein an amount of the solution further comprises hydrogen peroxide and acetic acid and the composition is substantially free of any surfactant. In some embodiments, the aqueous solution is substantially free of any isomer of lactic acid other than L-(+)-Lactic acid. In further embodiments of any of the above, the concentration of peracid (e.g., peroxyacetic acid) in the solution is from 30 to 300 ppm (w/w), 60 to 80 ppm (w/w), 50 to 200 ppm (w/w); 60 to 160 ppm (w/w), 120 to 160 ppm (w/w), or 140 to 160 ppm (w/w); and the concentration of 2-hydroxy-organic acid (e.g., lactic acid) in the solution is selected from 0.1% to 5% (w/w), 0.1% to 2%, 0.2% to 1%, 0.2% to 0.6%, or 0.1% to 0.5%, or about 2%, 3%, or 4%; and the pH is from between 2.5 and 6.0, 2.5 to 5.0, 2.8 and 3.2, 2.5 and 3.5, or 2.6 and 3.2. In other embodiments of the above the solution is for contacting the produce to be sanitized from 10, 20 or 30 seconds to 2 minutes or about 10, 20, 30 or 40 secs. In further embodiments, the concentration of peracid acid is from 30 to 100 ppm (w/w), and the concentration of the 2-hydroxy organic acid is from 0.3 to 2.0% (w/w). In a particularly preferred embodiment, the concentration of peracid is 70 to 80 ppm (w/w), and the concentration of the 2-hydroxy organic acid is from 0.2 to 0.4% (w/w). In other embodiments of any of the above, the solution is at a temperature of 35° F. to 45° F. or at ambient temperature. These aqueous solutions can be free or substantially free of surfactants including any or all of nonionic surfactants, cationic surfactants or anionic surfactants. Generally, low levels of hydrogen peroxide from 1 to 20 ppm, 5 to 15 ppm, or 7 to 12 ppm may be present in the solution. In some embodiments, any peracid of the 2-hydroxy organic acid formed from hydrogen peroxide or present in the aqueous solution can be present in an amount which is less than $\frac{1}{10}^{th}$, $\frac{1}{5}^{th}$, $\frac{1}{20}^{th}$, or $\frac{1}{50}^{th}$ the amount of the corresponding 2-hydroxyorganic acid in the solution. In preferred embodiment of the above, the peracid is peroxyacetic acid and the 2-hydroxyorganic acid is selected from one or more of tartaric acid, citric acid, malic acid, mandelic acid, and lactic acid. In a particularly preferred embodiment, of any of the above, the 2-hydroxy organic acid is lactic acid.

A catalyst, added to accelerate the rate at which the organic peracid reaches equilibrium, may optionally also be present in the solution according to the invention. Typical catalysts are strong acids, such as, sulfuric acid, sulfonic acids, phosphoric, and phosphonic acids. When the peracid solution is diluted to produce the desired peracid level, the catalyst may also be diluted. The presence of low levels of sulfuric acid, for example concentrations in the range of about 1 ppm to about 50 ppm, does not adversely affect the properties of the sanitizer composition.

Optionally, any of the solutions of the invention may further comprise an agent to reduce or suppress sudsing or foaming of the solution during use or contact with the produce. The solutions according to the invention may also be essentially free of any nonionic, anionic, and/or cationic surfactant and/or also be essentially free of any thickening agent.

The solutions according to the invention may also comprise a colorant to facilitate detection of the solution on the produce.

If anionic surfactants are to be added to the aqueous solutions of the invention they are preferably selected from food-safe materials known in the art, $C_{6-18}$ alkyl sulfates and/or sulfonates (e.g., sodium or potassium lauryl sulfate) and mixtures thereof. The alkyl sulfates are preferred, for antimicrobial effectiveness and palatability, especially as the sodium and/or potassium salts. Sodium dodecyl sulfate, or sodium lauryl sulfate, is a particularly preferred anionic surfactant.

In some embodiments, accordingly, the peracid is peroxyacetic acid, the organic acid is lactic acid, and the anionic surfactant is sodium lauryl sulfate. In other embodiments, the concentration of peracid acid in the solution is from 3 to 100 ppm (w/w), the concentration of 2-hydroxy organic acid in the solution is from 0.1% to 2% (w/w); and the concentration of the anionic surfactant in the solution is from 10 to 2500 ppm, and the pH is between 2.5 and 5.0. In a still further embodiment, the concentration of peracid is 5 to 100 ppm (w/w), the concentration of 2-hydroxy organic acid is 0.1 to 2% (w/w), and the concentration of anionic surfactant is 50 to 400 ppm.

Generally, the concentration of hydrogen peroxide in the aqueous solutions is 5-fold to 10-fold less that the concentration of the peracid and its presence reflects the equibilibrium or interconversion of the peracid with the corresponding acid and hydrogen peroxide. The concentration of the hydrogen peroxide can be for instance less than 5 ppm, 10 ppm or 20 ppm depending upon the selection and concentration of the peracid. Accordingly, the concentration of hydrogen peroxide in the aqueous solution is typically much less than that of the peracid.

Accordingly, in some embodiments, the invention provides an aqueous solution comprising i) an organic peracid of the formula RC(O)OOH wherein R is methyl, ethyl, n-propyl, or s-propyl; ii) a 2-hydroxy organic acid selected from tartaric acid, citric acid, malic acid, mandelic acid, and lactic acid; and, optionally, iii) an anionic surfactant; wherein the aqueous solution has a pH from 2.5 to 6.0, 4.0 to 6.0, 3.5 to 4.5, 3.0 to 5.0, 3.6 to 4.2, from 2.5 to 5.0, 2.5 to 4.5, 2.5 to 3.5, 2.7 to 3.5, 3.6 to 4.6, 2.8 to 3.2, inclusive, or about 3.0 (e.g., 3.0+/−0.2; 3.0+/−0.3); and the concentration of peracid is from 40 to 250 ppm (w/w) inclusive, and the concentration of the 2-hydroxy organic acid is from 0.1 to 1% (w/w), inclusive. In further embodiments, the aqueous solution has a peracid which is peroxyacetic acid and a 2-hydroxy organic acid which is is L-(+)-lactic acid. In still further embodiments, the concentration of the peroxyacetic acid in the solution is from 50 to 100 ppm (w/w), the concentration of the lactic acid in the solution is from 0.1% to 0.6% (w/w). A preferred aqueous solution has a concentration of peroxyacetic acid from 60 to 80 ppm (w/w) and a concentration of lactic acid of from 0.1% to 0.4% (w/w). In other embodiments of any of the above the pH falls in a range selected from 2.5 to 4.5, 2.8 to 3.2, 2.5 to 5.0, and 2.7 to 3.5. In other embodiments of any of the above, the solution is at a temperature of 35° F. to 45° F. or at ambient temperature. These aqueous solutions can be substantially free of surfactants including any or all of nonionic surfactants, cationic surfactants or anionic surfactants. Generally, low levels of hydrogen peroxide from 1 to 20 ppm, 5 to 15 ppm, or 7 to 12 ppm may be present in the solution. Any peroxy 2-hydroxy organic acid formed or present in the aqueous solution can be present in an amount which is less than $\frac{1}{10}^{th}$, $\frac{1}{5}^{th}$, $\frac{1}{20}^{th}$, or $\frac{1}{50}^{th}$ the amount of the corresponding 2-hydroxyorganic acid in the solution.

In some embodiments, the aqueous solution is formed by adding a solution of the 2-hydroxy organic acid which is substantially free of hydrogen peroxide to a solution of the peracid or by adding a solution of the peracid to a solution of the 2-hydroxy organic acid which is substantially free of hydrogen peroxide. The resulting mixture can be a concentrate or pre-blend as described above or in a sanitizing concentration suitable for contacting with produce as described herein. In other embodiments, the organic acid which is substantially free of any hydrogen peroxide and the peracid are added separately to an aqueous fluid used to wash or sanitize the produce. In some embodiments, the pH and/or the concentration of the peracid and/or the concentration of the 2-hydroxy organic acid in the solution is maintained by monitoring one or more of the pH, concentration of the peracid, concentration of the 2-hydroxy organic acid, or oxidation reduction potential of the solution and adding a concentrate or pre-blend of the aqueous solution to maintain the pH, the concentration of the peracid and lactic acid in the aqueous solution during use of the solution in contacting produce.

Any of the above solutions of the invention may in particular further comprise an agent to reduce or suppress sudsing or foaming of the solution during use or contact with the produce. The solutions according to the invention may also be essentially free of any nonionic and/or cationic surfactant and/or also be essentially free of any thickening agent.

In an additional embodiment, the aqueous solution of the invention has a concentration of peracid in the solution from about 60 to 80 ppm (w/w), a concentration of 2-hydroxy organic acid in the solution of from about 0.2% to 1.25% (w/w); and a concentration of anionic surfactant in the solution of from about 150 to 200 ppm (w/w), and a pH between about 3.8 and 4.2, inclusive or 3.8 and 4.2, inclusive.

The aqueous solutions according to the invention may also optionally include a sequestering agent that chelates metals that catalyze the decomposition of hydrogen peroxide. These agents include, but are not limited to, organic phosphonic acids capable of sequestering bivalent metal cations, as well as the water-soluble salts of such acids. A common chelant is 1-hydroxyethylidene-1,1-diphosphonic acid. The chelants present in the sanitizer composition are typically diluted upon use, thus minimizing their effect during use. In particular, an aqueous sanitizer solution of the invention can optionally contain an agent to chelate magnesium or calcium.

Without being wed to theory, the presence of the optional anionic surfactant may serve to reduce the surface tension and viscosity of the aqueous solution and facilitate the spread of the solution over the surface of the produce. The low viscosity improves the completeness of the treatment by promoting spreading over the surface of the food, especially where there are layers, rugosities, etc. The low viscosity also improves rinsing properties and the speed of any residual drying.

In some embodiments, the aqueous solution is capable of reducing a microbial contamination on the surface of the produce by at least 2 log units, more preferably, by at least 3 log units, and still more preferably by at least 4, log units according to any method as described in the Examples (e.g., using $E.\ Coli$ or $Listeria$ pathogen surrogates attached to lettuce leaves). In other embodiments, the method inhibits spoilage or prolongs shelf-life of the produce by 10%, 20%, 30, 40%, 20 to 50% or by 1, 2, 3, 4, or 5 days according to any method as described in the Examples.

In the United States of America, the use and selection of cleaning ingredients for the purpose of washing fruits and vegetables is described by the United States Code of Federal Regulations, Title 21, Section 173.315: "Ingredients for use in washing or lye peeling of fruits and vegetables". These regulations, which are incorporated herein by reference, set forth ingredients that can be used for direct contact with food and are described as "generally regarded as safe" (GRAS), and a few other selected ingredients. These sections also provide certain limitations on the amount of material that can be used in a given context.

Preferably, substances added directly to, or contacted with human food, can be chosen to be generally recognized as safe (GRAS) as incorporated above. Direct GRAS ingredients shall be used under current good manufacturing practice which includes that a direct human food ingredient be of appropriate food grade; that it be prepared and handled as a food ingredient, and that the quantity of the ingredient added to food does not exceed the amount reasonably required to accomplish the intended physical, nutritional, or other technical effect in the food item.

The solutions may be provided as a pre-blend or concentrate which is diluted with water to achieve a sanitizing solution for contacting with produce as described herein. Pre-blends or concentrates are contemplated which require a 4- to 200-fold, 10 to 100-fold, 10 to 50-fold, 10 to 25 fold, 4 to 10-fold dilution with water before use (e.g., about a 5-, 10-, 20-, 40-, 50, 100-fold dilution).

The term "substantially free" generally means the referenced substance is absent or present as a minor constituent which may not materially change the properties of the referenced material. With respect to hydrogen peroxide, a 2-hydroxy organic acid solution which is substantially free of hydrogen peroxide can be one which has no hydrogen peroxide or else has an amount of hydrogen peroxide which is less than 0.1 ppm (w/w). With respect to a peroxy 2-hydroxyorganic acid, a sanitizing solution is substantially free of the 2-hydroxy organic peracid if the 2-hydroxy organic peracid is absent in a referenced composition or is present in an amount which is less than $\frac{1}{10}^{th}$, $\frac{1}{20}^{th}$, $\frac{1}{40}^{th}$ or $\frac{1}{100}^{th}$ of that of the corresponding 2-hydroxy organic acid or is present only as a reaction product first formed by a reaction of the 2-hydroxy organic acid in solution containing hydrogen peroxide and an organic peracid of the formula RC(O)OOH wherein R is methyl, ethyl, n-propyl, or s-propyl. Accordingly, in some embodiments, the sanitizing composition or 2-hydroxy organic acid solution used in the making of the sanitizing composition is substantially free of a peracid of the 2-hydroxy organic acid.

Containers and Kits

In some embodiments, the invention provides a kit comprising the aqueous sanitizing solution according to the invention and instructions for its use in the treatment of produce. In some further embodiments, the kit provides a first part comprising a peracid solution that is at or near equilibrium. Typically the solution is provided ready to use or else comprises about 5% to about 35% by weight of a peracid, such as peroxyacetic acid, or mixture of peracids and comes with instructions as to how much it should be diluted with water prior to use. The kit contains a soaking bowl and strainer. The ready-to-use formulation may be provided in a spray bottle. In other embodiments, the kit may provide the aqueous sanitizing solution as a concentrate in one container along with a re-fillable spray bottle optionally containing an amount of the ready-to-use formulation. This kit would include directions as to the appropriate factor of dilution to use when bringing up the concentrate with water. Typically, the concentrate would be 4, 5, 6, 8, 10 or 20-fold more concentrated than the ready to use formulation. Such kits would be especially suitable for consumer use.

Methods of the Invention

In a second aspect, the invention provides a method of treating produce, said method comprising contacting the surface with an aqueous sanitizing solution according to the invention. The solution can be contacted or applied to the produce by any suitable means as known to persons of ordinary skill in the art. For instance, the solution can be applied by any method that insures good contact between the surface to be sanitized and the sanitizer solution. Such methods include bathing, washing, coating, brushing, dipping, immersing, wiping, misting, spraying, and fogging. These steps may be repeated to assure a thorough contacting. Once applied, after a residence time sufficient to assure the desired degree of sanitizing action (e.g., 4, 5, 6, 7, or 8 log fold-removal of a microbial contaminant), the solution may be physically removed from the surface of the produce by centrifugation and/or draining/and/or rinsing or washing the produce with water suitable for use on foods (e.g., potable water). Any combination of these steps may be performed in any order. The rinsing is not essential where the peracid, 2-hydroxy organic acid, and sodium lauryl sulfate are present in GRAS amounts. In particular, the peracids preferably used are volatile and, hence, would leave little residue on the produce upon drying.

The residence time will vary with the concentration of the peracid (e.g. peroxyacetic acid), the 2-hydroxyorganic acid (e.g., L-(+)-lactic acid, and the surfactant (if any). However, generally, it is contemplated that the surface of the produce may be contacted with the aqueous sanitizer solution for a residence time of from about 10 seconds to about 10 minutes. More preferably, the residence time is from about 20 seconds up to about 1, 2 or 4 minutes. The residence time can vary in accordance with the temperature and concentration of the peracid and 2-hydroxyorganic acid. Lower temperatures and concentrations would require longer contact times as could be readily empirically determined by a person of ordinary skill in the art.

The temperature at which the aqueous sanitizer solution/rinse solution is applied should be in accordance with the thermal tolerance of the produce. Generally, cooler temperatures prolong the shelf-life of produce. Accordingly, the sanitizer solution can be effectively applied at temperatures between 35° F. and 60° F. Preferably, the temperature is between 38° F. and 45° F. Most preferably, the temperature is from 38° F. to about 42° F. However, other temperatures can be used in accordance with the heat tolerance of the produce being treated.

In some embodiments, the contacting reduces a microbial contamination on the surface of the produce by at least 4 log units, more preferably, by at least 5 log units, and still more preferably by at least 6, 7, or 8 log units. In other embodiments, the method inhibits spoilage or prolongs shelf-life of the produce by 10%, 20%, 30, 40%, 20 to 50% or by 1, 2, 3, 4, or 5 days. The contaminant can be human pathogen (e.g., a strain of E. coli O157H7, Listeria monocyogenes, Salmonella) or an indigenous microorganism typically found on the surface of produce.

The aqueous sanitizing solution according to the invention can be used for both domestic and commercial applications, such as in the food service, food processing, and health care industries. Although the sanitizer composition is especially used on food and food-contact surfaces it can also be used on other contact surfaces. In particular embodiments, the solutions according to the invention are used to treat produce before, during or after transport, while on display, during storage, or shortly before meal preparation and/or consumption.

The method is especially suitable for treating fruits and vegetables, including especially those which may be to eaten uncooked. For example, without limitation, the method can be practiced on spring mix, arugula, radicchio, pea shoots, dill, chives, spinach, Romaine lettuce, asparagus, head lettuce, leaf lettuce, Iceberg lettuce, endive, parsley, spinach, radishes, celery, carrots, beets, onions, rhubarb, eggplant, peppers, cucumbers, tomatoes, potatoes, sweet potatoes, turnips, rutabagas, zucchini, cabbage, kale, kohlrabi, collard greens, cauliflower, Brussels sprouts, okra, mushrooms, snow pea, soybean, broccoli, snapdragon pea, corn, and dandelion greens; fruits such as apples, cantaloupe, pineapple, watermelon, honeydew, orange, lemon, tangerine, peaches, cherries, apricots; quince, plums, grapes, and pears; and berries such as strawberries, raspberries, gooseberries, loganberries, boysenberries, cranberries, currants, elderberries, blackberries, and blueberries; and herbs.

In some embodiments, the microbial contaminant to be reduced by the treatment is a human pathogen (e.g., enterotoxic bacterium), including but not limited to, a bacterium (e.g., E. coli O157H7, Listeria moncytogenes, Salmonella), virus, a fungus, or a mold. In other embodiments, the microbial contaminant is one which can hasten the spoilage or decay of produce.

It has also been surprisingly found that the co-formulation of the peracid (e.g., peroxyacetic acid) with the 2-hydroxy organic acid (e.g., L-(+)-lactic acid) in the aqueous sanitizer composition provides a particularly effective and long-lasting sanitizer composition when in use. When used to treat produce, the composition has to be refreshed or supplemented with additional peracid and 2-hydroxyorganic acid at a much lower rate to maintain a concentration of the peracid in a range of from about 60 to 80 ppm and the lactic acid in a concentration of from 0.2 to 0.4%, or about 2.5%.

In some embodiments, the sanitizing composition is provided as an aqueous pre-blend mixture (e.g., about a 5-200-fold concentrate, a 5-, 10-, 20-, 40-, 50- or 100-fold concentrate) to be added to the water to be contacted with the produce. In some embodiments, the concentration of peracid and/or 2-hydroxyorganic acid is adjusted in the wash solution to maintain their concentration(s) by addition of the pre-blend or concentrate based upon the concentration of the peracid and/or 2-hydroxy organic acid in the wash solution as determined by actual measurement or historical consumption data.

In commercial applications, in some embodiments, the produce is transported to the wash solution where the produce is contacted with the sanitizing solution by immersion in the solution. Air bubbles can be generated to facilitate the contacting and/or the mixing of a pre-blend. The produce is then removed from the sanitizing solution, optionally rinsed by spraying with water free of a peracid and 2-hydroxy organic acid/and or by being immersed in water free of a peracid and 2-hydroxy organic acid. The rinse water can be further removed by shaking of the produce or centrifugation of the produce which may optionally be further air dried to remove any excess moisture.

The following examples are intended to illustrate, but not limit, the invention.

Examples

Example 1

Figure 2:
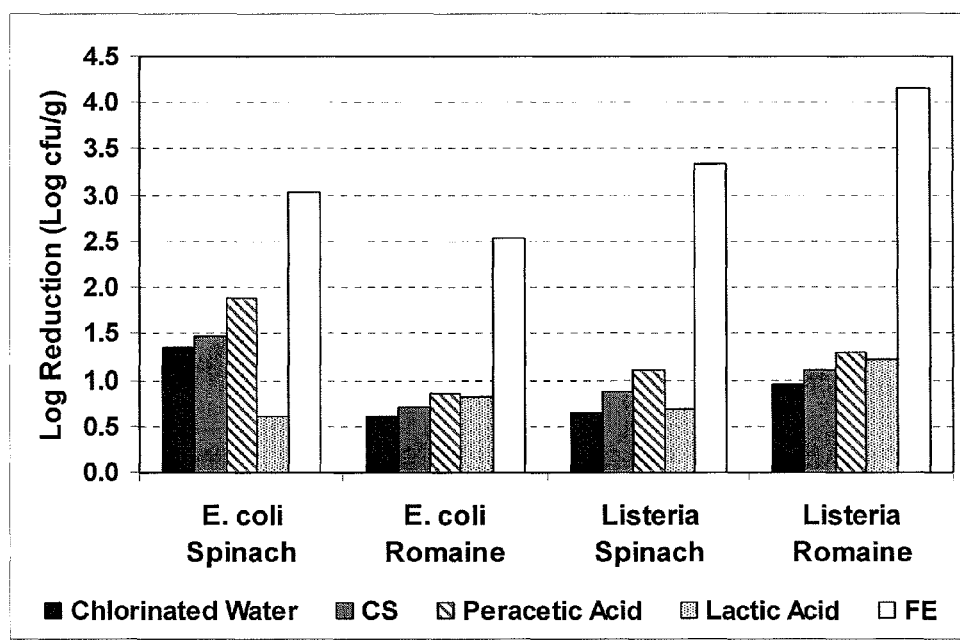
FIG. 2 is a comparison of each of the five treatments of FIG. 1 in a leaf-attached cell challenge test.
Figure 3:
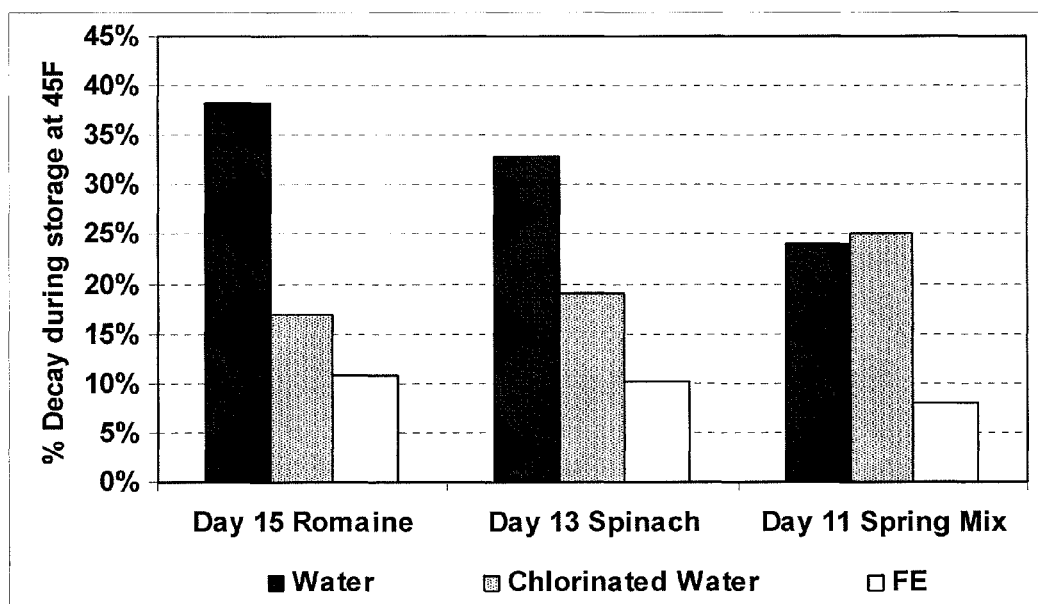
FIG. 3 is a comparison of the ability of chlorinated water and an aqueous solution according to the invention (FE: peroxyacetic acid, lactic acid and sodium lauryl sulfate) to reduce the decay of treated produce.
Figure 4:
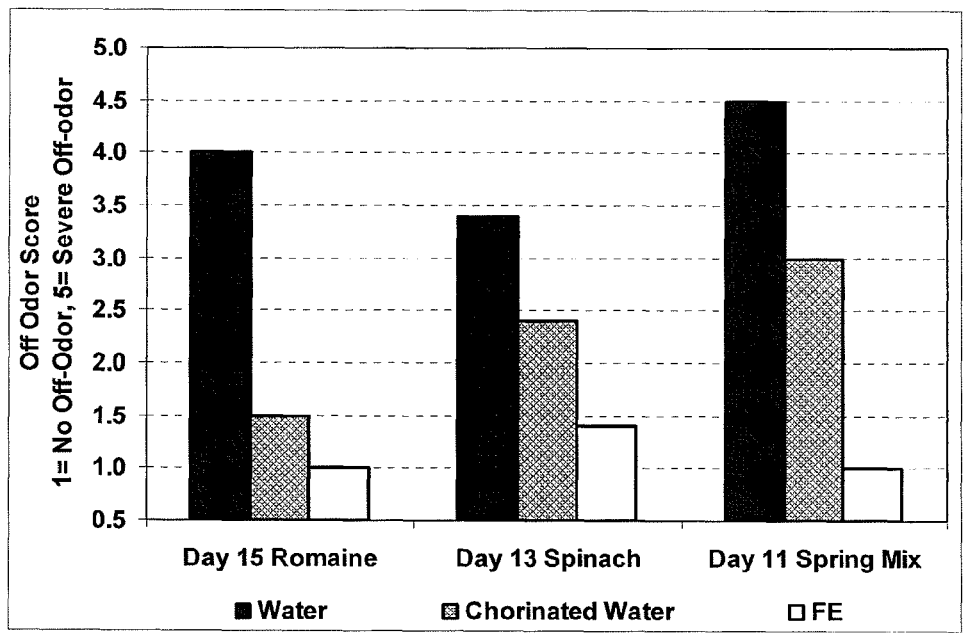
FIG. 4 is a comparison of the ability of chlorinated water and an aqueous solution according to the invention (FE: peroxyacetic acid, lactic acid and sodium lauryl sulfate) to reduce off-odor in treated produce.
Figure 5:
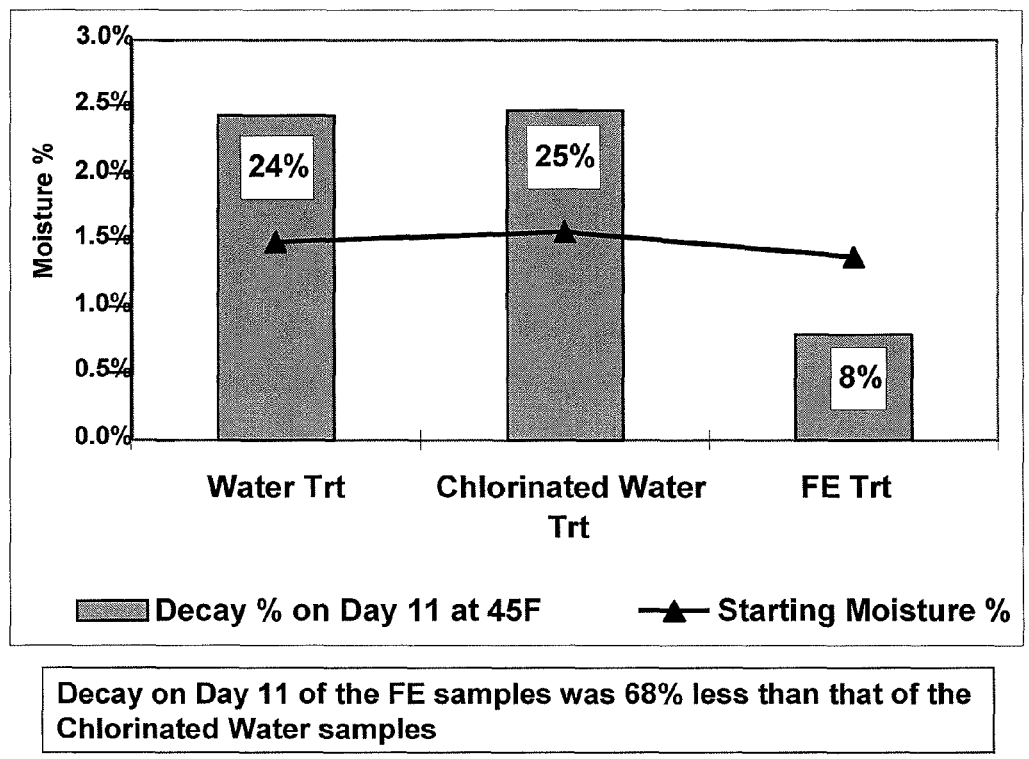
FIG. 5 is a comparison of the ability of chlorinated water and an aqueous solution according to the invention (peroxyacetic acid, lactic acid and sodium lauryl sulfate) to reduce the decay of Spring Mix with a low-moisture content.
Figure 6:
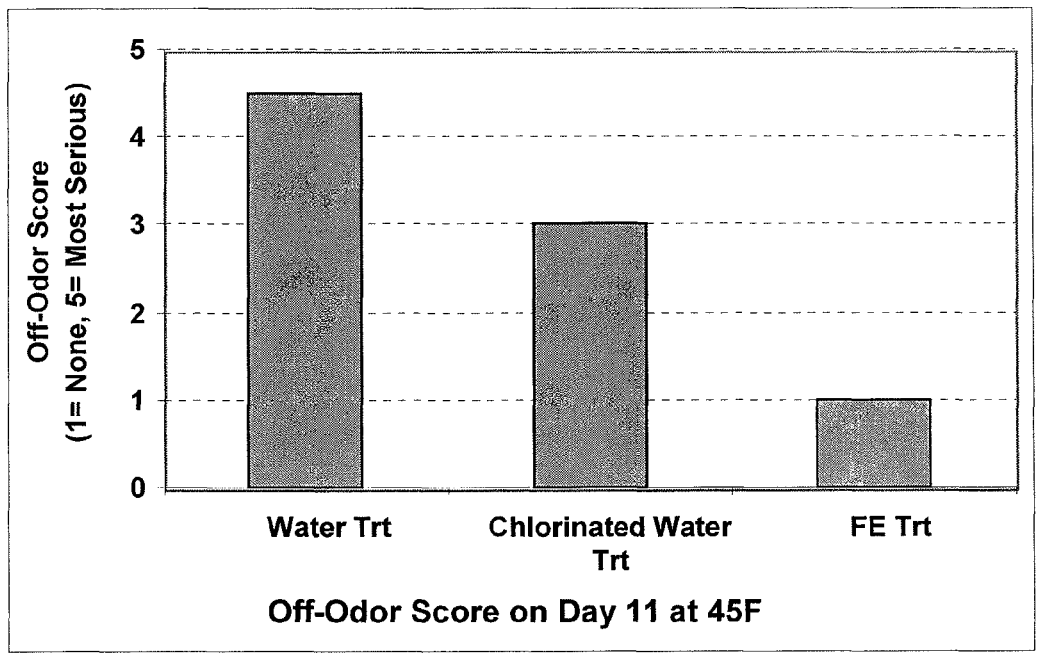
FIG. 6 is a comparison of the ability of treatment with chlorinated water or an aqueous solution according to the invention (peroxyacetic acid, lactic acid and sodium lauryl sulfate) to reduce off-odor in a Spring Mix with a low-moisture content.
Figure 7:
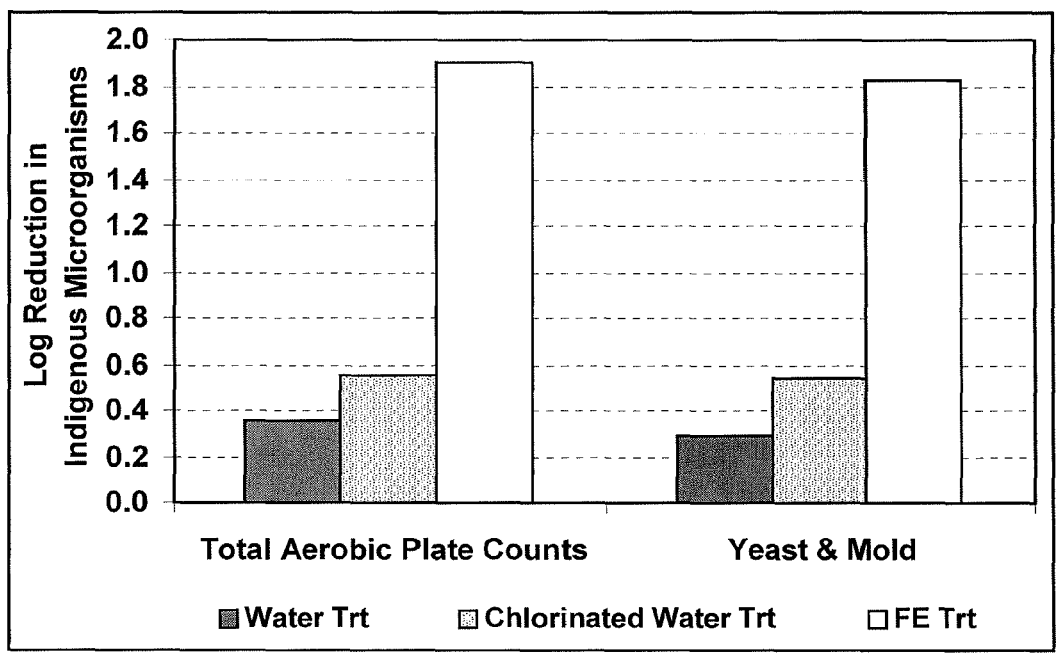
FIG. 7 is a comparison of the ability of chlorinated water and an aqueous solution according to the invention (peroxyacetic acid, lactic acid and sodium lauryl sulfate) to inhibit the growth of indigenous microorganisms in a Spring Mix with a low-moisture content.
Figure 8:
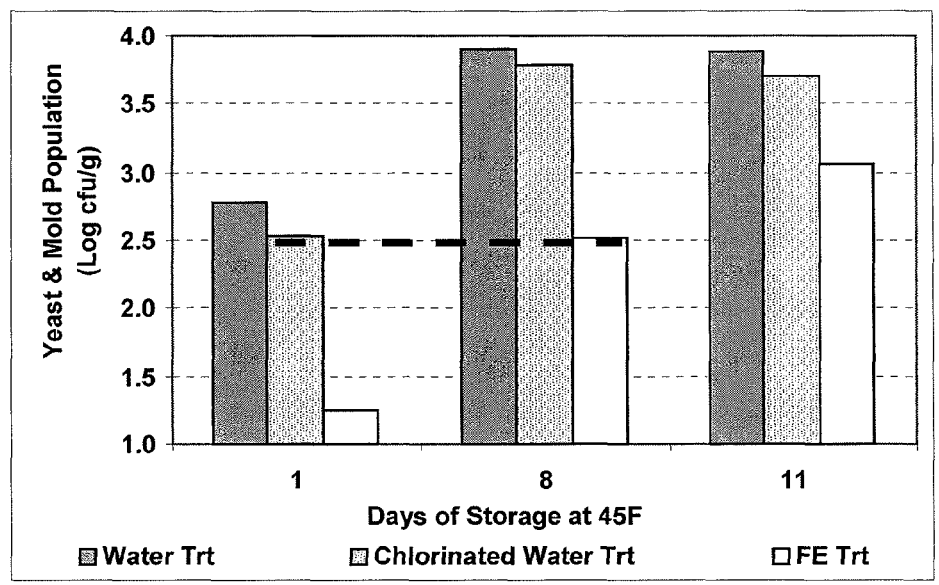
FIG. 8 is a comparison of the ability of chlorinated water and an aqueous solution according to the invention (peroxyacetic acid, lactic acid and sodium lauryl sulfate) to inhibit spoilage in a Spring Mix with a low-moisture content.
Figure 9:
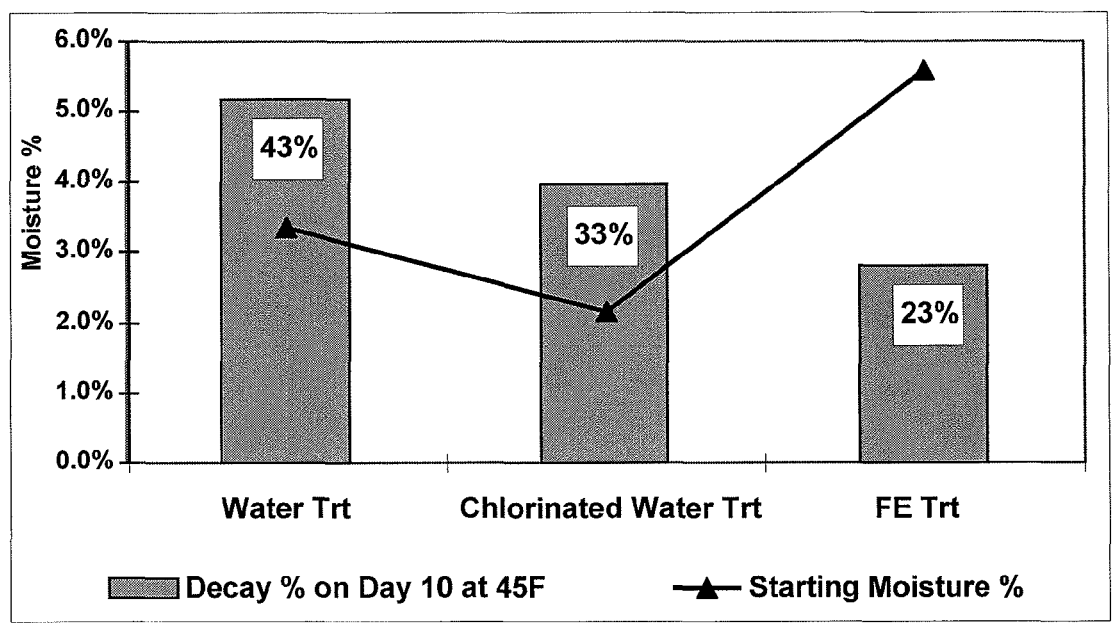
FIG. 9 is a comparison of the ability of chlorinated water and an aqueous solution according to the invention (peroxyacetic acid, lactic acid and sodium lauryl sulfate) to reduce the decay of Spring Mix with a high-moisture content.
Figure 10:
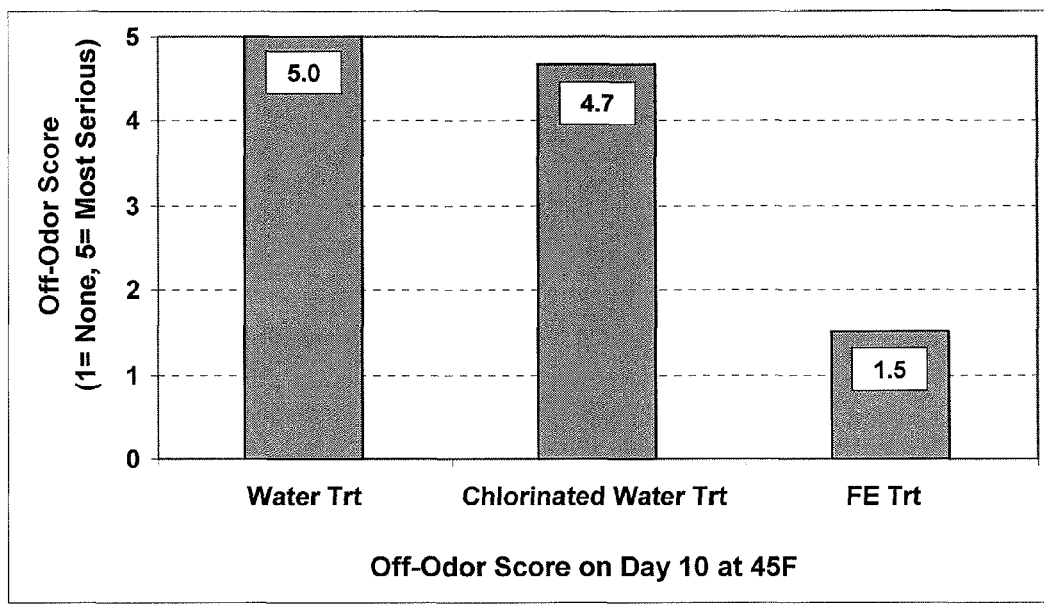
FIG. 10 is a comparison of the ability of treatment with chlorinated water or an aqueous solution according to the invention (peroxyacetic acid, lactic acid and sodium lauryl sulfate) to reduce off-odor in a Spring Mix with a high-moisture content.
Figure 11:
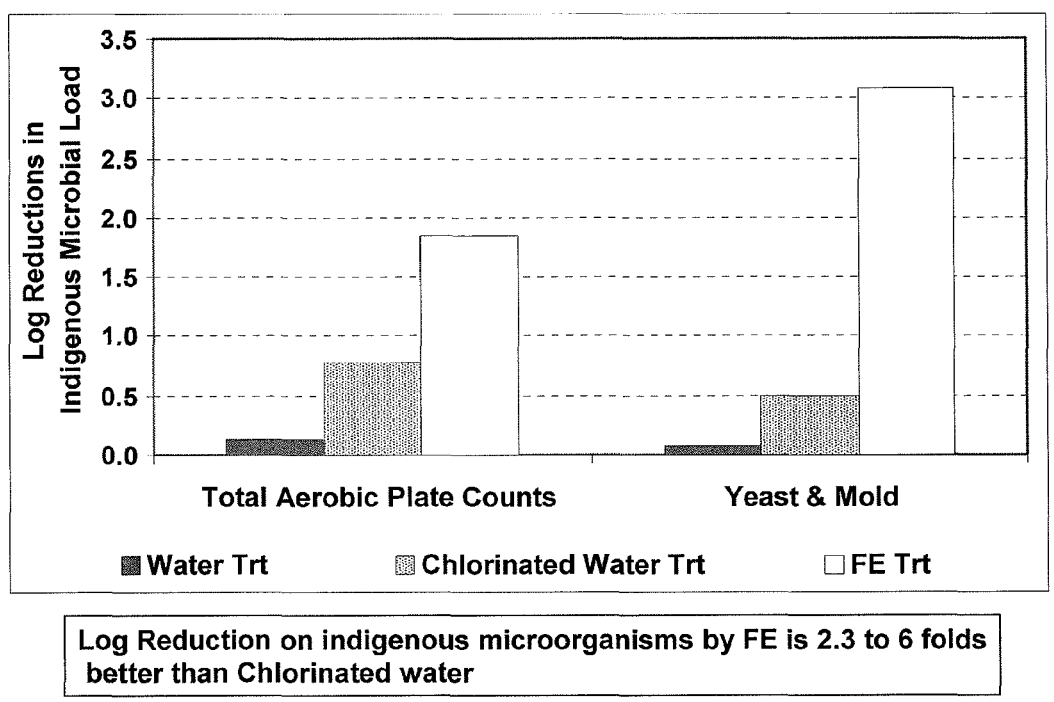
FIG. 11 is a comparison of the ability of chlorinated water and an aqueous solution according to the invention (peroxyacetic acid, lactic acid and sodium lauryl sulfate) to inhibit growth of indigenous microorganisms in a Spring Mix with a high-moisture content.
Figure 12:
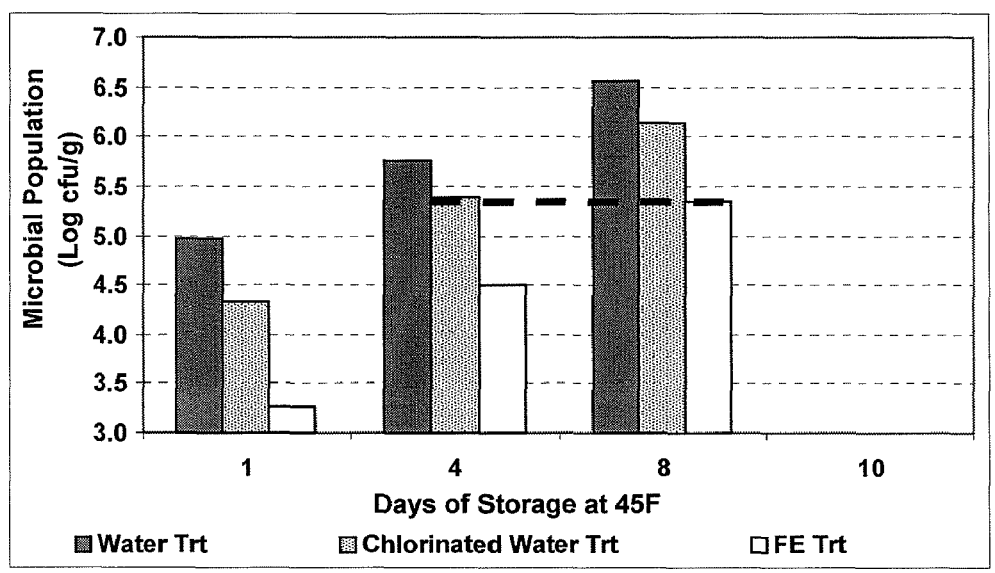
FIG. 12 is a comparison of the ability of chlorinated water and an aqueous solution according to the invention (peroxyacetic acid, lactic acid and sodium lauryl sulfate) to inhibit spoilage in a Spring Mix with a high-moisture content.
Figure 13:
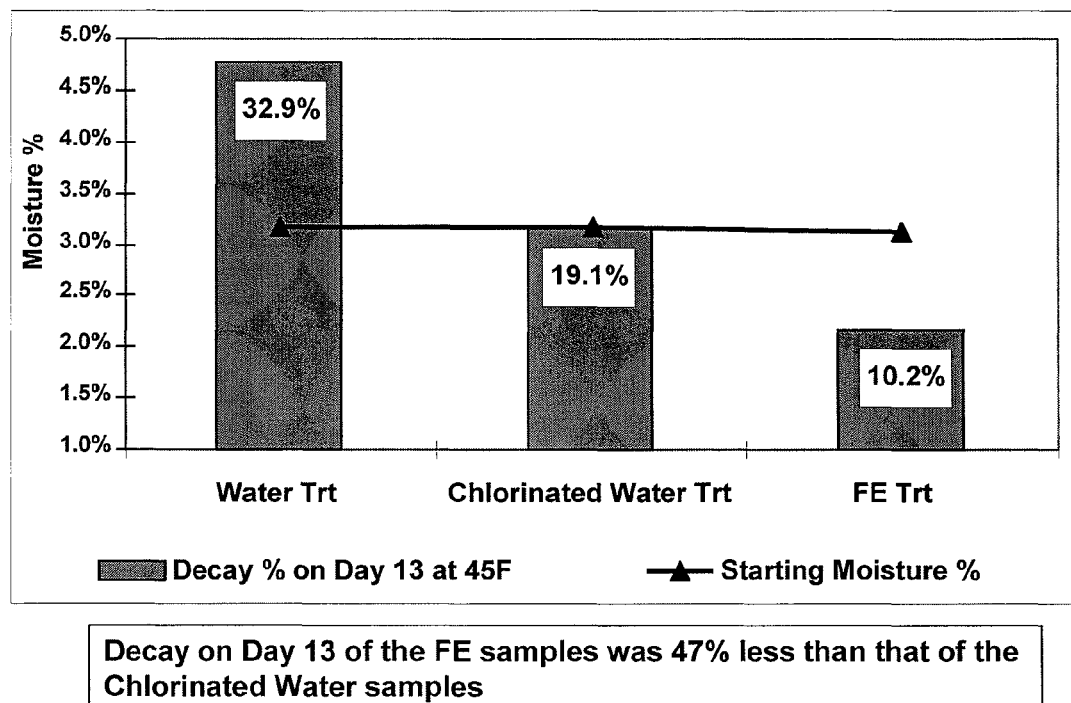
FIG. 13 is a comparison of the ability of chlorinated water and an aqueous solution according to the invention (peroxyacetic acid, lactic acid and sodium lauryl sulfate) to reduce the decay of spinach.
Figure 14:
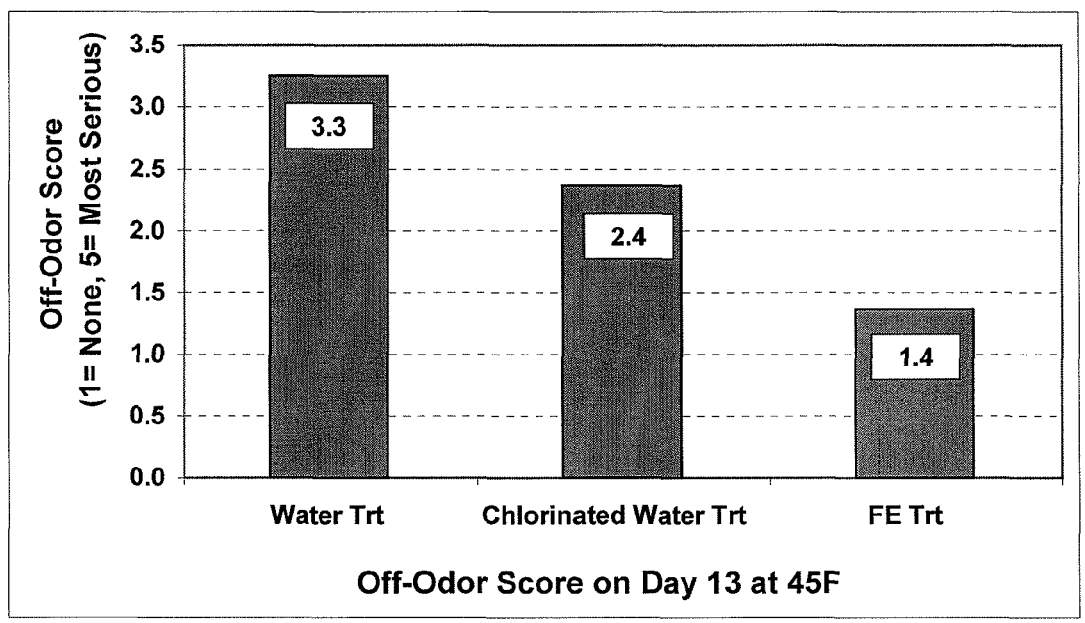
FIG. 14 is a comparison of the ability of treatment with chlorinated water or an aqueous solution according to the invention (peroxyacetic acid, lactic acid and sodium lauryl sulfate) to reduce off-odor in spinach.
Figure 15:
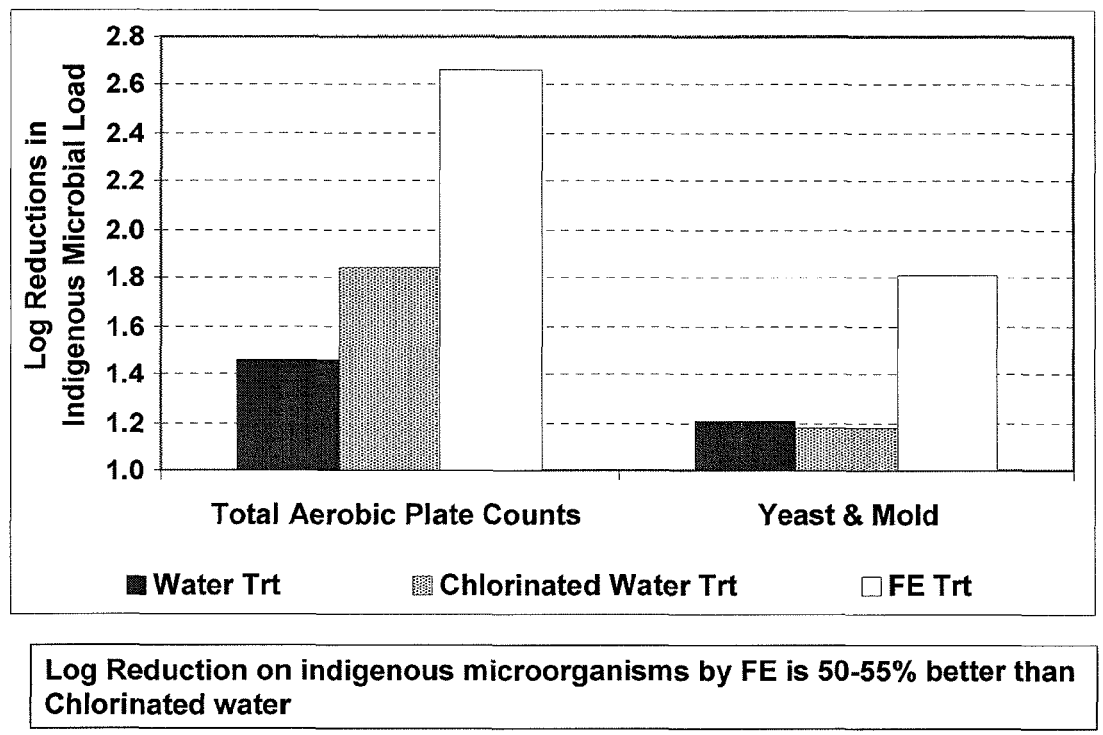
FIG. 15 is a comparison of the ability of chlorinated water and an aqueous solution according to the invention (peroxyacetic acid, lactic acid and sodium lauryl sulfate) to inhibit the growth of indigenous microorganisms in spinach with a high-moisture content.
Figure 16:
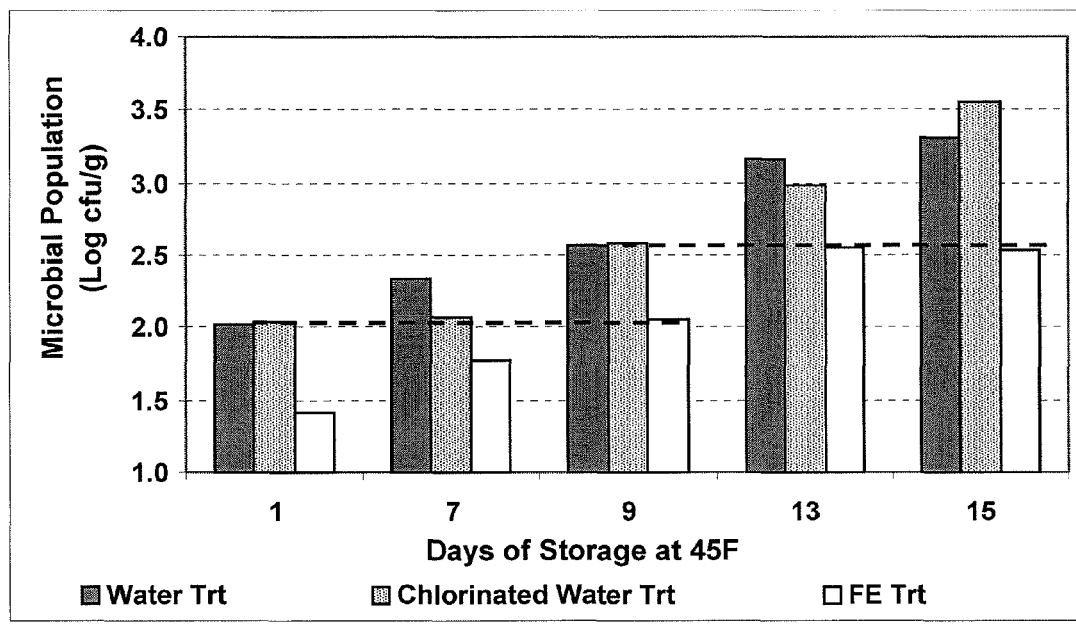
FIG. 16 is a comparison of the ability of chlorinated water and an aqueous solution according to the invention (peroxyacetic acid, lactic acid and sodium lauryl sulfate) to inhibit spoilage microorganisms in spinach.

The present example illustrates the use of an aqueous sanitizing solution according to the invention. As illustrated in FIGS. 1 to 16, the solutions according to the invention advantageously remove microorganisms from the surface of a variety of produce, inhibit the growth of indigenous microorganisms on the treated produce, and can remove model pathogens from the surface of the produce. The methods and compositions of the invention are also shown to greatly improve the shelf-life of the produce and greatly retard produce decay. The findings extend to such diverse microorganisms as bacteria, yeast, and mold.

A. Standard Operating Procedure for Shelf Life Study

This method can be used to determine the shelf life of produce that has been treated by a sanitizing solutions, generally and, particularly, those according to the invention.

Preparation

Cooled eight 20-gallon containers with 75% water to ~45° F. Autoclave twelve 5-gallons tubs wrapped well in tin foil at least 1 day in advance of processing.

1. Depending on the type of produce, use the corresponding OTR tubes; cut, marked, and sealed to form bags. Place the bags under an UV light in the biological safety cabinet for 2 h to minimize contamination.

Processing

1. Formulate chemical sanitizers immediately before usage. All calculations are based on mass/mass.
2. Fill containers to ¾ full only so as to prevent overflowing during processing
3. Place raw product gently into a stainless steel basket with lid and fill it to ¾ full.
4. Start the timer when the basket is submerged into the chemical sanitizer
5. Cycle up and down the filled basket gently for 30 s
6. Remove the treated basket with produce from the container with chemical solution and immediately transfer it into another container ¾ filled with water for rinsing
7. Cycle up and down 10 times in water to remove the majority of residual chemical on the treated produce surface
8. Place the basket with the treated produce in an inverted manner and empty the contents gently into a dryer bin liner
9. Repeat Steps '3' to '8' until there the dryer bin liner is full. Closed the dryer lid and centrifuge for 20 min
10. Empty the dried produce from the bin liner to sterile tubs and let the dried treated produce sit for an extra 10-15 minutes for moisture equilibration with the environment to achieve the same moisture content as the corresponding production facility.
11. Clean all tools, equipment, and containers
12. Repeat Steps '1' to '11' for other sanitizer treatments Bagging and Sealing
1. Tare the scale with the bag every time.
2. Fill the bag with the target produce mass
3. Seal bags with a proper sealing machine
4. Store in boxes at 45 F and perform evaluations: microbiological analysis, Open Bag Evaluation (OBE), visual inspection on the appropriate days of interest.

Evaluations
1. Use the appropriate forms for OBE.
2. Visually inspect the produce and photographs the differences of the samples from various chemical
   a. OBE moisture determination—weigh initial mass of leaves, spread leaves onto folded paper towels and blot dry by pressing hands to remove exterior moisture and take a final weight.

Calculations:
Volume to be used of a stock solution with a concentrated solution:

$$M_{stock} = \frac{[Desired]M_{desired}}{[Stock]}$$

Moisture difference:

$$\text{Difference} = (M_{befire}) - (M_{after})$$

Moisture Percentage:

$$\%_{moisture} = \frac{(M_{befire}) - (M_{after})}{(M_{before})}$$

3. For visual analysis be sure that bags are labeled before first analysis to follow the same bags throughout shelf-life
4. Enumerate microbial population of the treated produce using serial dilution and spread plating
5. Samples for microbial and OBE analysis may be retrieved, for instance, on days 1, 5, 7, 9, 12, and 15.

B. Standard Operating Procedure for Suspended Cells Challenge Test

This procedure is used to determine the antimicrobial activity of sanitizers on microorganisms that are suspended in a liquid.

Processing Parameters and Treatments
1. Temperature: 45 F
2. Residence time: 30−/−10 secs
   pH: 3+/−0.3
3. Pathogen surrogates: *E. coli* K12, *Listeria innocua*
4. Spoilage microorganisms surrogates: *Pseudomonasflourescens, Saccharomyces cerevisiae*

Running the Test
1. Transfer 1.00 mL of a $10^8$ cfu/g stock culture into a test tube containing 9.00 gm of tested solution
2. Vortex the mixture for 15 s
3. Stop the reaction by transferring 1 mL of the treated samples to 9 mL of Butterfield Phosphate Buffer
4. Enumerate viable residual cells through serial dilutions and spread plating
5. Ensure that the operating temperature is kept at 45±1° F. (only one test tube is removed out of the fridge at a time as the kinetics of chemicals change significantly if the whole test is run at room temperature)

C. Standard Operating Procedure for Attached Cells Challenge Test

This method can be used to determine the antimicrobial activity of sanitizers on microorganisms that are attached on the surface of leaves Processing Parameters and Treatments
1. Temperature: 45° F.
2. Residence time: 45 s
3. pH: 3+/−0.3
4. Treatments: water, chlorinated water, CS, lactic acid, peroxyacetic acid, FE sanitizer (i.e., here, aqueous solutions comprising peroxyacetic acid and lactic acid) at 16 levels
5. Products tested: Romaine, spinach, spring mix
6. Pathogen surrogate: *E. coli* K12, *Listeria innocua*
7. Microorganisms tested: indigenous microorganisms on produce leaves (Total aerobic plate counts [APC], yeast, and mold [YM])

Sample Preparation
1. Take 3-4 leaves of the tested produce and place them into a 6"×6"×5" sterile polypropylene (PP) basket. If the tested produce is Romaine, cut the Romaine into 2"×4" rectangles
2. Retrieve 1.00 mL of the $10^8$ cfu/g stock culture with a 1-mL pipette-man and slowly spike the leaves surface by dropping small size droplets of the innoculum onto the leaf surface. Be careful not to shake the PP basket and causes the droplets to fall out of the leaves prior to drying
3. Let the basket with the spiked leaves sit in a biological safety cabinet with a fan running (~0.5 W.C.) for 1.75 hrs
4. Remove the PP baskets with spiked leaves from the cabinet and transfer them into a cold room/refrigerator at 40-45° F. for 0.25 hrs Treatment of Spiked Leaves
1. Place a PP basket with spiked leaves into a sterile container containing 3-L of 45 F water for 45 seconds with swirling
2. Rinse immediately for 10 seconds by dipping the treated basket into tap water at 45 F
3. Take treated leaves from the basket and place them into a stomacher bag by means of a sterile tong
4. Label the stomacher bag with the associated treatment for the leaves
5. Repeat the Step 1 to 4 with the other treatments of the test Enumeration of Treated Leaves
1. Add phosphate buffer into a stomacher bag with the treated leaves until a 10-fold dilution is attained
2. Stomach the bag with phosphate buffer and treated leaves for 30 seconds
3. Shake the leaves back into the phosphate buffer solution and repeat the stomaching for another 30 seconds
4. Remove buffer from stomached sample and enumerate for residual cells by serial dilution and spread plating
5. Repeat Step 1 to 4 for all other treatments D. Standard Operating Procedure for Preparation of Microbial Stock Culture This procedure is used to prepare a $10^8$-$10^9$ cfu/mL stock culture for suspended and attached cells challenge tests. The cell concentration of the stock culture is enumerated prior to testing solution.
1. Activation of Stock Culture
   a. All procedures are done in a sterile environment (e.g. inside a Biological Safety Cabinet)

b. A loop of cells is retrieved from the pure stock culture by means of a sterile loop. The loop of cells is aseptically transferred into a test tube with 10-mL of sterile growth medium (broth).
c. Step "b" is repeated 3 times
d. Incubate inoculated tubes from Step "b" and "c" for 2 days under an optimal growing temperature for the microorganism to be activated
e. Step "b" to "d" is referred to as the first transfer ($1^{st}$ T) f. Retrieve 0.1-mL of growth medium from a test tube of the $1^{st}$ T and aseptically transfer it into another test tube with 10-mL of sterile growth medium
g. Verify that the tube from $1^{st}$ T has pure culture by spread plating a 50 to 100-uL sample of growth medium onto an agar plates
h. Repeat Step "g" 2 times
i. Incubate both the plates and transfer tubes #2 for two days at selected optimum temperature
j. Steps "f" to "i" are referred to as $2^{nd}$ T
k. Repeat Steps "f" to "i" with 100 mL growth medium for the $3^{rd}$ T
l. Store the resulted Erlenmeyer culture flasks from $3^{rd}$ T in refrigerator overnight
m. Take the $3^{rd}$ T flask from Step "1" and transferred it equally into 4 centrifuge tubes
n. Centrifuge the tubes with pure stock culture at 10,000 RPM for 10 minutes
o. Decant immediately the growth medium. A pellet of cells would be formed at the bottom of the centrifuged tube
p. Add the same amount of sterile de-ionized water to the pellet of cell
q. Vortex to loosen and re-suspend the pellet of cells
r. Repeat Step "n" and "o" two more times
s. To obtain a final $10^8$-$10^9$ cfu/gm of suspended cell culture, add 1/10 of the initial volume of sterile de-ionized water to the cell pellet of Step "r"
t. Consolidate all the re-suspended cell cultures into one centrifuge tube to form the final suspended stock culture The effects of a sanitizing solution according to the invention on the removal of microbes on the surface of produce.

Results

The following tables show the results of the suspended-cells challenge tests with and without surfactant:

| Listeria | Suspended Concentration | Surfactant Log Reductions PAA (ppm) | | |
|---|---|---|---|---|
| | | 60 | 70 | 80 |
| | | | | No |
| LA (%) | 0.6% | 3.4 | 5.0 | >8.4 |
| | 0.9% | 4.5 | 6.0 | >8.4 |
| | 1.2% | 4.9 | 6.0 | >8.4 |
| | | | | Yes |
| LA (%) | 0.6% | 6.3 | 7.7 | >9.0 |
| | 0.9% | 7.7 | 7.5 | >9.0 |
| | 1.2% | 7.6 | 8.0 | >9.0 |
| Water | Control | 0.0 | | |
| Chlorine | 64 ppm | 2.1 | | |
| CS | 0.6% | 3.2 | | |

| | Suspended Concentration | Surfactant Log Reductions PAA (ppm) | | |
|---|---|---|---|---|
| | | 60 | 70 | 80 |
| E. Coli | | | | No |
| LA (%) | 0.6% | 5.6 | 6.2 | 6.6 |
| | 0.9% | 6.1 | 7.3 | 8.7 |
| | 1.2% | 7.2 | 8.5 | >9 |
| Listeria | | | | Yes |
| LA (%) | 0.6% | 5.6 | 6.6 | 6.8 |
| | 0.9% | 6.2 | 8.4 | >9 |
| | 1.2% | 8.4 | 9.1 | >9 |
| Water | Control | 0.0 | | |
| Chlorine | 64 ppm | 3.7 | | |
| CS | 0.6% | 6.1 | | |

The following tables show the results for the attached-cells challenge test:

| E. Coli | Attached Concentration | Spinach PAA (ppm) | | | |
|---|---|---|---|---|---|
| | | 0 | 60 | 70 | 80 |
| LA (%) | 0.0% | 0.00 | 0.69 | 1.33 | 2.46 |
| | 0.6% | 0.09 | 0.65 | 1.70 | 2.94 |
| | 0.9% | 0.42 | 1.37 | 1.92 | 3.70 |
| | 1.2% | 0.81 | 1.82 | 2.37 | 4.17 |
| Chlorine | 64 ppm | 1.35 | | | |
| CS | 0.6% | 1.47 | | | |

| E. Coli | Attached Concentration | Romaine PAA (ppm) | | | |
|---|---|---|---|---|---|
| | | 0 | 60 | 70 | 80 |
| LA (%) | 0.0% | 0.05 | 0.26 | 0.53 | 1.18 |
| | 0.6% | 0.24 | 0.47 | 0.76 | 1.68 |
| | 0.9% | 0.37 | 1.06 | 1.39 | 2.60 |
| | 1.2% | 1.28 | 1.25 | 1.64 | 4.51 |
| Chlorine | 64 ppm | 0.61 | | | |
| CS | 0.6% | 0.71 | | | |

| Listeria | Attached Concentration | Spinach PAA (ppm) | | | |
|---|---|---|---|---|---|
| | | 0 | 60 | 70 | 80 |
| LA (%) | 0.0% | 0.0 | 0.3 | 0.5 | 1.2 |
| | 0.6% | 0.1 | 0.3 | 1.6 | 3.0 |
| | 0.9% | 0.2 | 0.3 | 2.0 | 3.5 |
| | 1.2% | 0.2 | 0.7 | 3.9 | 3.9 |
| Chlorine | 64 ppm | 0.4 | | | |
| CS | 0.6% | 0.5 | | | |

| | Attached | Romaine PAA (ppm) | | | |
|---|---|---|---|---|---|
| Listeria | Concenration | 0 | 60 | 70 | 80 |
| LA (%) | 0.0% | 0.0 | 0.6 | 1.0 | 1.7 |
| | 0.6% | 1.1 | 0.9 | 2.3 | 4.1 |
| | 0.9% | 1.4 | 1.6 | 3.2 | 4.5 |
| | 1.2% | 1.5 | 2.2 | 4.1 | 4.8 |
| Chlorine | 64 ppm | 1.0 | | | |
| CS | 0.6% | 1.2 | | | |

The above results accord with a surprisingly effective and striking increase in the removal of microorganisms and improvement of product shelf-life associated due to use of an aqueous solution according to the invention.

Example 2

The next example demonstrates that the presence of a 2-hydroxy organic acid (e.g., lactic acid) greatly reduces the consumption of peroxyacetic acid during the treatment of produce and illustrates the use of an aqueous sanitizing solution according to the invention. As shown below, the solutions according to the invention advantageously conserve peroxyacetic acid during the removal of microorganisms from the surface of a variety of produce. The methods and compositions of the invention are also shown to greatly improve the shelf-life of the produce and greatly retard produce decay. The savings should extend to such diverse microorganisms as bacteria, yeast, and mold.

Synergism with Respect to Efficacy in a Suspended Cells Challenge Test at 20 s Residence Time with No Surfactant.

The experimental treatment groups were tap water, chlorinated water, a FE sanitizer wash water (FE, FE sanitizer, a solution of peroxyacetic acid and lactic acid, as further specified in a given experiment). The experimental parameters were 40 to 45° F.; the residence time was 20 s; the pH:
  water (~7)
  chlorinated water (6.5 to 7.1)
  lactic acid (3.8 to 4.0)
  peroxyacetic acid (6.5 to 6.8)
  FE sanitizer wash water (2.7 to 3.2)
The microbial surrogates were Listeria innocua or E. coli K-12 with a streptomycin resistance gene.

The experimental protocol was as follows:
1. Transfer 1.00 mL of a ~10^8 cfu/g Lactobacillus plantarum (ATCC 14917) stock culture into a test tube containing 9.00 mL of treatment test solution
2. Vortex the mixture for 15 s
3. Stop the reaction by transferring 1 mL of the treated samples to 9 mL of Butterfield Phosphate Buffer
4. Enumerate viable residual cells through serial dilutions and spread plating with 1-mL transfers
5. Ensure that the operating temperature is kept at 40 to 45° F. (only one test tube is removed out of the fridge at a time as the kinetics of chemicals change significantly if the whole test is run at room temperature)
6. Repeat Steps 1 to 5 two more times
7. Repeat Steps 1 to 6 with flume water
8. Repeat Steps 1 to 6 with chlorinated water
9. Repeat Steps 1 to 8 with various levels of FE
10. Repeat Steps 1 to 8 with various levels of lactic acid
11. Repeat Steps 1 to 8 with various levels of peroxyacetic acid
12. Repeat Steps 1 to 11 with Listeria innocua (ATCC33090)

Estimation of Log Reductions
1. Log activation is a measure of the percent of microorganisms that are inactivated during the disinfection process and is defined as Log Inactivation=$\text{Log}_{10}(N_o/N_T)$ where $N_o$ is the initial influent concentration of viable microorganisms; $N_T$ is the concentration of surviving microorganisms. As M cfu/g=microbial population of stock culture; W cfu/g=microbial population in solution of "Water Treatment" and X cfu/g=microbial population in solution of "X Treatment," the Log reduction caused by "Treatment X"=Log (w/x)

Results and Conclusions

TABLE 2.1

Comparison of log reduction of suspended Listeria innocua cells by chlorinated wash water, lactic acid wash water, peroxyacetic acid wash water, and FE sanitizer wash water
Listeria innocua ATCC 33090
20 s Residence time

| Lactic Acid (ppm) | Peroxyacetic acid (ppm) | | | |
|---|---|---|---|---|
| | 0 | 70 | 75 | 80 |
| 0 | | 1.40 | 1.70 | 1.80 |
| 2000 | 0.08 | 3.11 | 4.09 | 5.15 |
| 2500 | 0.19 | 3.22 | 5.03 | 5.36 |
| 3000 | 0.05 | 3.49 | 5.04 | 7.15 |
| Chlorinated Water, ~15.5 ppm, ~pH 7 | | | | 0.06 |

TABLE 2.2

Comparison of log reduction of suspended Lactobacillus plantarum cells by chlorinated wash water, lactic acid (LA) wash water, peroxyacetic acid (PA) wash water, and FE sanitizer wash water.
Lactobacillus plantarum 14917
20 s Residence time

| Lactic Acid (ppm) | Peroxyacetic acid (ppm) | | | |
|---|---|---|---|---|
| | 0 | 70 | 75 | 80 |
| 0 | | 4.52 | 5.59 | 5.59 |
| 2000 | 0.00 | 7.09 | >7.74 | >7.74 |
| 2500 | 0.02 | 7.09 | >7.74 | >7.74 |
| 3000 | 0.01 | >7.74 | >7.74 | >7.74 |
| Chlorinated Water, ~15.5 ppm, ~pH 7 | | | | 0.00 |

Log reduction of the test FE sanitizer (here, a combination of lactic acid and peroxyacetic acid as specified above) on L. innocua and L. plantarum was significantly better than PA wash water and LA wash water. This clearly indicated the synergistic effects of combining LA and PA. FE sanitizer wash water with 70 ppm PA and 2000 ppm LA at 20 s residence time provided ~3-$\log_{10}$ reduction on Listeria innocua. The log reduction of provided by the combination of lactic acid and peroxyacetic acid) was about significantly 2 to 4 folds better than peroxyacetic acid with no lactic acid addition.

Example 3

The next experiments compares the effects of sanitizers on vegetative pathogens suspended in a liquid.
Processing Parameters and Treatments
  Treatments: tap water, chlorinated water, FE sanitizer wash water;

Temperature: 40 to 45° F.; Residence time: 30 s pH:
   water (~7)
   chlorinated water (6.5 to 7.1)
   FE sanitizer wash water (2.7 to 3.2)
Pathogens:
   5-strains cocktail of *E. coli* O157:H7 (F4546, F4637, SEA13B88, TW14359, 960218)
   5-strains cocktail of *Listeria monocytogenes* (ATCC 19115, ATCC51414, ATCC15313, FRR B2472 (SCOTT A), 1838)
5-strains cocktail of *Salmonella* (*S. Newport, S. Tennessee, S. muenchen, S cubana, S. St. Paul*)

Activation of Stock Culture
1. Activation of stock culture is attained via a series of transfers of stock culture to optimum growth medium aseptically in a biological safety cabinet
2. Retrieve a small loop (~100 uL) of pure culture from the stock culture in storage and transfer it into a test tube containing 10 mL of optimum growth medium broth specific for each microorganism as recommended by American Type Culture Collection (ATCC) or published articles
3. Incubate culture till it reaches end of log growth phase at its optimum growth temperature as recommended by ATCC or published articles
4. Verify purity of the transferred culture by streak plating and spread plating
5. Retrieve 1.5-ml of culture broth from Step 3 and transfer it into a 250-mL Erlenmeyer Flask containing 150-mL optimum growth medium broth specific for each microorganism as recommended by American Type Culture Collection (ATCC) or published articles
6. Incubate culture till it reaches end of log growth phase at its optimum growth temperature as recommended by ATCC or published articles
7. Verify purity of the transferred culture by streak plating
8. Enumerate the concentration of the culture broth from Step 6 by spread plating and serial dilution at 1-mL transfers
9. Cool down the 150-Ml Erlemneyer Flask stock culture at refrigeration temperature for 1 to 4 h prior to inoculation Innoculum Preparation and Enumeration
1. Separate the 150-mL of cooled-down stock culture in the $2^{nd}$ transfer Erleumeyer flask into three 50-mL centrifuge tubes at equal volume (50 mL each)
2. Centrifuge the tubes at 10,000 RPM for 15 minutes at 4° C.
3. Decant the liquid broth from each centrifuge tube leaving behind the pellet of cells
4. Fill the centrifuge tube from Step 3 with 5-mL of sterile 0.1% peptone water and vortex to loosen and mix the pellet of cells
5. Pour all the re-suspended stock culture into one centrifuge tube to form a ~$10^8$ cfu/gm of innoculum Enumerate and confirm the microbial population of the innoculum obtained from Step '5' by spread plating via serial dilutions with 1-mL transfers Methods
6. Transfer 1.00 mL of a ~$10^8$ cfu/g *E. coli* O157:H7 5-strains cocktail stock culture into a test tube containing 9.00 mL of test solution
7. Vortex the mixture for 15 s
8. Stop the reaction by transferring 1 mL of the treated samples to 9 mL of Butterfield Phosphate Buffer
9. Enumerate viable residual cells through serial dilutions and spread plating with 1-mL transfers
10. Ensure that the operating temperature is kept at 40 to 45° F. (only one test tube is removed out of the fridge at a time as the kinetics of chemicals change significantly if the whole test is run at room temperature)
11. Repeat Steps 1 to 5 two more times
12. Repeat Steps 1 to 6 with flume water
13. Repeat Steps 1 to 6 with chlorinated water (10 ppm active chlorine at pH 6.5 to 7)
14. Repeat Steps 1 to 8 with another level of FE
15. Repeat Steps 1 to 8 with another 5-strains cocktail of *Listeria monocytogenes*
16. Repeat Steps 1 to 8 with another 5-strains cocktail of *Salmonella*

Results and Conclusion

TABLE 3.1

Comparison of Log reduction of suspended *E. coli* O157:H7 cells by chlorinated wash water and the test FE sanitizers wash waters.

| 5-Strains cocktail of *E. coli* O157:H7 | Microbial population (log cfu/mL) | Log Reduction |
|---|---|---|
| Residence time | 30 s | |
| Test Date | Jan. 21, 2009 | |
| Temperature | 40 to 45 F. | |
| Inoculum microbial population | 9.0 | |
| Tap Water | 8.0 | |
| (9 mL water with 1 mL of inoculum) | | |
| Chlorinated Water, 10 ppm at pH 7.1 | 7.0 | 0.9 |
| (9 mL chorinated water with 1 mL of inoculum) | | |
| FE1-PA: 68 ppm, LA; 4600 ppm, pH 2.8 to 3 | <1.0 No residual cells at $10^1$ | >7 |
| (9 mL FE sanitizer with 1 mL of inoculum) | | |
| FE2-PA: 71 ppm, LA 5100 ppm, pH 2.8 to 3 | <1.0 No residual cells at $10^1$ | >7 |
| (9 mL FE sanitizer with 1 mL of inoculum) | | |

TABLE 3.2

Comparison of Log reduction of suspended *Salmonella* cells by chlorinated wash water and the test FE sanitizers wash water.

| 5-Strains cocktail of *Salmonella* | Microbial population (log cfu/mL) | Log Reduction |
|---|---|---|
| Residence time | 30 s | |
| Test Date | Jan. 21, 2009 | |
| Temperature | 40 to 45 F. | |
| Inoculum microbial population | 8.9 | |
| Tap Water | 8.0 | |
| (9 mL water with 1 mL of inoculum) | | |
| Chlorinated Water, 10 ppm at pH 7.1 | 7.0 | 1.0 |
| (9 mL chorinated water with 1 mL of inoculum) | | |
| FEI-PA: 68 ppm, LA; 4600 ppm, pH 2.8 to 3 | <1.0 No residual cells at $10^1$ | >7 |
| (9 mL FE sanitizer with 1 mL of inoculum) | | |
| FE2-PA: 71 ppm, LA 5100 ppm, pH 2.8 to 3 | <1.0 No residual cells at $10^1$ | >7 |
| (9 mL FE sanitizer with 1 mL of inoculum) | | |

TABLE 3.3

Comparison of Log reduction of suspended *Listeria monocytogenes* cells by chlorinated wash water and the test FE sanitizers wash water.

| 5-Strains cocktail of *Listeria moncytogenes* | Microbial population (log cfu/mL) | Log Reduction |
|---|---|---|
| Residence time | 30 s | |
| Test Date | Jan. 21, 2009 | |
| Temperature | 40 to 45 F. | |
| Inoculum microbial population | 7.1 | |
| Tap Water (9 mL water with 1 mL of inoculum) | 6.2 | |
| Chlorinated Water, 10 ppm at pH 7.1 (9 mL chorinated water with 1 mL of inoculum) | 5.0 | 1.2 |
| FE1-PA: 68 ppm, LA; 4600 ppm, pH 2.8 to 3 (9 mL FE sanitizer with 1 mL of inoculum) | No residual cells at $10^1$ | >5.2 |
| FE2-PA: 71 ppm, LA 5100 ppm, pH 2.8 to 3 (9 mL FE sanitizer with 1 mL of inoculum) | No residual cells at $10^1$ | >5.2 |

10 ppm chlorinated water reduced the populations of each pathogen by ~1-$\log_{10}$ when compared to the tap water control. The two concentrations of FE sanitizer wash water plate counts had no residual colonies and the results were recorded as <1.0 $\log_{10}$ cfu/mL. Hence FE sanitizer wash water delivered reductions of greater than 7-$\log_{10}$ for *E. coli* O157:H7 and *Salmonella*, and greater than 5.2-$\log_{10}$ for *Listeria monocytogenes* when compared to the tap water control. The lower reduction observed in *Listeria monocytogenes* does not indicate that the FE sanitizer was less effective against that pathogen as the reported results were restricted by the original population of the stock inoculum.

Example 4

The purpose of these experiments was to determine the antimicrobial activity of sanitizers on vegetative pathogens that are attached on the surface of leaves Processing Parameters and Treatments Treatments: tap water, chlorinated water, test FE sanitizer wash water;

Temperature: 40 to 45° F.; Residence time: 30 s;

pH:
water (~7)
chlorinated water (6.5 to 7.1)
FE sanitizer wash water (2.7 to 3.2)

Products tested: diced Romaine leaves and matured spinach leaves

Pathogens:
5-strains cocktail of *E. coli* O157:H7 (F4546, F4637, SEA13B88, TW14359, 960218)
5-strains cocktail of *Listeria monocytogenes* (ATCC 19115, ATCC51414, ATCC15313, FRR B2472 (SCOTT A), 1838)
5-strains cocktail of *Salmonella* (*S. Newport, S. Tennessee, S. muenchen, S cubana, S. St. Paul*)

Activation of Stock Culture

1. Activation of stock culture is attained via a series of transfers of stock culture to optimum growth medium aseptically in a biological safety cabinet.
2. Retrieve a small loop (~100 uL) of pure culture from the stock culture in storage and transfer it into a test tube containing 10 mL of optimum growth medium broth specific for each microorganism as recommended by American Type Culture Collection (ATCC) or published articles.
3. Incubate culture till it reaches end of log growth phase at its optimum growth temperature as recommended by ATCC or published articles.
4. Verify purity of the transferred culture by streak plating and spread plating.
5. Retrieve 1.5-ml of culture broth from Step 3 and transfer it into a 250-mL Erleumeyer Flask containing 150-mL optimum growth medium broth specific for each microorganism as recommended by American Type Culture Collection (ATCC) or published articles
6. Incubate culture till it reaches end of log growth phase at its optimum growth temperature as recommended by ATCC or published articles.
7. Verify purity of the transferred culture by streak plating.
8. Enumerate the concentration of the culture broth from Step 6 by spread plating and serial dilution at 1-mL transfers.
9. Cool down the 150-Ml Erlenmeyer Flask stock culture at refrigeration temperature for 1 to 4 h prior to inoculation.

Innoculum Preparation and Enumeration

1. Separate the 150-mL of cooled-down stock culture in the 2nd transfer Erlenmeyer flask into three 50-mL centrifuge tubes at equal volume (50 mL each).
2. Centrifuge the tubes at 10,000 RPM for 15 minutes at 4° C.
3. Decant the liquid broth from each centrifuge tube leaving behind the pellet of cells
4. Fill the centrifuge tube from Step 3 with 5-mL of sterile 5% Horse Serum solution and vortex to loosen and mix the pellet of cells.
5. Pour all the re-suspended stock culture into one centrifuge tube to form a ~108 cfu/gm of innoculum.
6. Enumerate and confirm the microbial population of the innoculum obtained from Step '5' by spread plating via serial dilutions with 1-mL transfers Samples Preparation 1. Take 4 leaves of the tested produce and place them into a 6"×6"×5" sterile polypropylene (PP) basket. If the tested produce is Romaine, cut the Romaine into 1.5"×2.5" rectangles
2. Of the four leaves in Step 1, two should have their upper epidermis facing upward and two should have their lower epidermis facing upward
3. Retrieve 50 uL of the ~$10^8$ cfa/g stock culture with a 100 uL pipette and slowly spike each leaf by dropping small size droplets (10 to 15 droplets) of the inoculum onto the leaf flat surface and midrib that are facing upward. Be sure to remove excess stock on sides of pipette tip before spiking leaves. Be careful not to shake the PP basket and causes the droplets to fall out of the leaves prior to drying.
4. Arrange the baskets with the spiked leaves in a biological safety cabinet with Drierite as shown in Photo 1 for 1-1.5 hrs at 70-80F and 38 to 48% relative humidity. Ensure that the hood temperature is steady (<±2F) throughout the drying process.
5. Ensure that the leaves are not in wilted condition at the end of the drying period.

Treatment of Spiked Leaves

Transfer 3 L of Test Solution from the PP Carboy into the 5-L Sterile PP Tub

1. Add the required volume of the final ingredient into the 3 L solution and mix thoroughly with a sterilized tong if needed
2. Transfer two spiked leaves (1 spiked on the upper epidermis and the other spiked on the lower epidermis) into an empty sterile PP basket
3. Place the PP basket with spiked leaves into a sterile container containing 3 L of the completed formulation of the test solution 4. Maintain the temperature of the test solution at 40-45° F.

5. Use a tong to gently pushed the leaves into the test solution to ensure total submersion of the leaves at all times and to prevent folding and overlapping of leaves 6. Start stop watch for timing the 30 s once the leaves are totally submerged 7. Take treated leaves from the basket and place them into a stomacher bag by means of a sterile tong 8. Label the stomacher bag with the associated treatment for the leaves 9. Smashed the leaves into pieces by means of a sanitized rubber melon hammer 10. Repeat Step 1 to 7 with the other treatments of the test 11. Each treatment must be done in triplicates following the sequence of Step 13

12. Each replicate must be performed separately to avoid error from bacterial death during the drying process. The order of testing is as followed:
   a. $1^{st}$ Replication: 1 sample of control with no spike, control with spiked bacteria, spiked bacteria with water wash, spiked bacteria with chlorinated water wash, spiked bacteria with FE1 wash, and spiked bacteria with FE2 wash.
   b. $2^{nd}$ Replication: 1 sample of control with no spike, control with spiked bacteria, spiked bacteria with water wash, spiked bacteria with chlorinated water wash, spiked bacteria with FE1 wash, and spiked bacteria with FE2 wash.
   c. $3^{rd}$ Replication: 1 sample of control with no spike, control with spiked bacteria, spiked bacteria with water wash, spiked bacteria with chlorinated water wash, spiked bacteria with FE1 wash, and spiked bacteria with FE2 wash.

13. Enumeration of samples must be performed immediately after each replication

Enumeration of Treated Leaves

1. Add 100 mL phosphate buffer into a stomacher bag with the treated mashed leaves until a 100-fold dilution is attained 2. Stomach the bag with phosphate buffer and treated leaves for 30 s 3. Shake the leaves back into the phosphate buffer solution and repeat the stomaching for another 30 seconds 4. Remove buffer from stomached sample and enumerate for residual cells by serial dilution and spread plating with 1-mL transfers 5. Repeat Step 1 to 4 for all other treatments Estimation of Log Reductions M cfu/g=microbial population on leaves without any treatment;

R cfu/g microbial population in water solution for the "Water Treatment";

W cfu/g=microbial population on leaves from "Water Treatment";

X cfu/g=microbial population on leaves from "X Treatment";

Hence, Log reduction caused by "Treatment X"=Log (w/x)

Microorganisms removed due to mechanical washing=R

Microorganisms died during the drying process=M−W−R

Results

TABLE 4.1

Log reduction of pathogens attached on spinach and Romaine lettuce (average of 3 replicates) by tap water at 40 to 45° F.

|  | Tap Water Wash |
| --- | --- |
| *E. coli* O157:H7 on Spinach | 0.8 |
| *E. coli* O157:H7 on Romaine | 1.5 |
| *Salmonella* on Spinach | 0.9 |
| *Salmonella* on Romaine | 0.3 |
| *L. monocytogenes* on Spinach | 1.4 |
| *L. monocytogenes* on Romaine | 1.4 |

The tap water wash removed 0.3 to 1.5 $\log_{10}$ of inoculated cells from the leaves indicating that complete attachment of cells on the leaves was not achieved. This was probably caused by the desiccation and wilting of the leaves under low relative humidity of the environment (20 to 23% rather than 38 to 48% as listed in the protocol).

TABLE 4.2

Additional log reduction of pathogens attached on spinach and Romaine lettuce (average of 3 replicates) by chlorinated wash water when compared with tap water wash

|  | Chorinated water wash water at 40-45 F. | | |
| --- | --- | --- | --- |
|  |  | Concentration | |
|  | pH | ppm | Log Reduction |
| *E. coli* O157:H7 on Spinach | 7.1 | 9.7 | 2.3 |
| *E. coli* O157:H7 on Romaine | 7.0 | 9.7 | 1.4 |
| *Salmonella* on Spinach | 6.9 | 9.3 | 1.2 |
| *Salmonella* on Romaine | 6.9 | 9.7 | 0.8 |
| *L. monocytogenes* on Spinach | 6.9 | 9.3 | 0.1 |
| *L. monocytogenes* on Romaine | 6.9 | 9.0 | 0.4 |

The 10 ppm chlorinated water provided an additional reduction of 0.1-$\log_{10}$ to 1.4-$\log_{10}$ on the pathogens. The 2.3-$\log_{10}$ in the case of spinach was exceptionally high when compared with surrogate attached cells results and was probably caused by the incomplete attachment of the cells on the leaves as shown by the tap water wash results.

TABLE 4.3

Additional log reduction of pathogens attached on spinach and Romaine lettuce (average of 3 replicates) by FE sanitizer wash water at 40 to 45 F.

|  | FE sanitizer wash water at 40-45 F. | | |
| --- | --- | --- | --- |
|  | Peroxyacetic acid conc. (ppm) | Lactic acid conc (ppm) | Log Reduction |
| *E. coli* O157:H7 on Spinach | 68 | 4846 | 2.9 |
| *E. coli* O157:H7 on Romaine | 67 | 4800 | 2.6 |
| *Salmonella* on Spinach | 66 | 4833 | 2.3 |
| *Salmonella* on Romaine | 69 | 4758 | 2.1 |
| *L. monocytogenes* on Spinach | 70 | 4782 | 2.2 |
| *L. monocytogenes* on Romaine | 71 | 4769 | 3.4 |

The test FE sanitizer wash water (69 ppm peroxyacetic acid and 4800 ppm lactic acid) provided an additional reduction of 2.1-$\log_{10}$ to 3.4-$\log_{10}$ on the pathogens when compared with tap water wash.

When compared to chlorinated water, the FE sanitizer provided an additional 2-$\log_{10}$ reduction of pathogens that were attached on leaves. In addition, storing the spread plates at 40

F indicated that injured cells were not able to grow at refrigerated temperatures within a week. If the bacterial cells were not able to grown on nutrient rich agar plates, they will most likely not grow on the treated fresh produce.

Example 5

These experiments evaluated the consumption or depletion of peroxyacetic acid when used to wash produce. The objective accordingly was to compare the amount of chopped Romaine Lettuce required to deplete 600 gallons of chlorinated wash water, 600 gallons of peroxyacetic acid wash water, and 600 gallons of FE sanitizer wash water Processing Parameters and Treatments
Treatments: chlorinated water, peroxyacetic acid wash water, and FE sanitizer wash water
Temperature: 38 to 40° F.
Residence time: 20 s
pH:
chlorinated water (6.5 to 7.1)
peroxyacetic acid (6.5 to 6.8)
FE sanitizer wash water (2.7 to 3.2)
Produce: 1.5"×2" diced Romaine lettuce A. Determination of the Amount of Romaine Lettuce that could Deplete 600 Gallons of Peroxyacetic Acid Wash Water.
1. Perform full sanitization on the Pilot Line System.
2. Fill the $2^{nd}$ flume tank, $2^{nd}$ reservoir, and $2^{nd}$ filtering tank with tap water.
3. Recycle the water through the system until the water in the system is being cooled down to 40° F.
4. Calibrate the Prominent System and use the Prominent System to monitor the concentration of PAA in the wash water.
5. Add the PAA to the $2^{nd}$ filtering tank until the target processing limit is reached.
6. Dice the Romaine Lettuce via the translicer.
7. Collect the 2"×2" diced Romaine in totes.
8. Record the weight of each tote prior to transferring it to the $2^{nd}$ flume.
9. Collect three untreated bags of Romaine Lettuce from each bin (1 top, 1 middle, and 1 bottom).
10. Collect three treated bags of Romaine Lettuce at the end of F2 (1 beginning, 1 middle, and 1 end of the bin).
11. Place white totes at the bottom of the locations with water spill. Return the spilt water back into the flume tank as needed.
12. Place white totes at the bottom outlets of the centrifuge to collect liquid that would be spin off from the leaves. Return the collected water back into the flume tank as needed.
13. Repeat Steps 'e' to 'k' for the rest of the bins till the FE concentrations fall below the lowest processing limits.
14. Enumerate the microbial population (APC and Yeast and mold) on the collected samples.

B. Determination of the Amount of Romaine Lettuce that could Deplete 600 Gallons of FE Wash Water
1. Perform full sanitization on the Pilot Line System.
2. Fill the $1^{st}$ flume tank, $2^{nd}$ flume tank, $1^{st}$ reservoir, $2^{nd}$ reservoir, $1^{st}$ filtering tank, and 2nd filtering tank with tap water.
3. Recycle the water through the system until the water in the system is being cooled down to 40° F.
4. Switch on the by-passes for the $1^{st}$ and $2^{nd}$ flume tank systems so that water would not be going through the filtering systems but only recycling from the flume tank to its associate reservoir continuously.
5. Add the chemical ingredients to both tank until the target processing limit is reached.
6. Verify the concentration of FE by the probe of the Prominent Monitoring System at the $1^{st}$ flume tank (F1), $1^{st}$ Reservoir (R1), $2^{nd}$ Flume tank (F2), and the $2^{nd}$ Reservoir (R2).
7. Collect water samples from F1 and F2.
8. Assemble the Romaine Lettuce Bins next to the dumpster.
9. Transfer whole Romaine Lettuce leaves from the bin to the conveyor.
10. Ensure that the lid above the F1 is closed. Turn the "ON/OFF" switch of the translicer to "ON".
11. Turn the conveyor for transferring leaves into the translicer to "ON".
12. Ensure that the chopped Romaine are delivered evenly into the flume tank without aggregation and clumping.
13. Collect three untreated bags of Romaine Lettuce from each bin (1 top, 1 middle, and 1 bottom).
14. Collect three treated bags of Romaine Lettuce at the end of F2 (1 beginning, 1 middle, and 1 end of the bin).
15. Verify the pH, temperature, and the concentration of FE at the $1^{st}$ flume tank (F1), $1^{st}$ Reservoir (R1), $2^{nd}$ Flume tank (F2), and the $2^{nd}$ Reservoir (R2) before and after processing a bin.
16. Place white totes at the bottom of the locations with water spill. Return the spilt water back into the flume tank as needed.
17. Place white totes at the bottom outlets of the centrifuge to collect liquid that would be spin off from the leaves. Return the collected water back into the flume tank as needed.
18. Repeat Steps 'e' to 'o' for the rest of the bins till the FE concentrations fall below the lowest processing limits.
19. Enumerate the microbial population (APC and Yeast and mold) on the collected samples.

c. Determination of the Amount of Romaine Lettuce that could Deplete 600 Gallons of Chlorinated Water to Concentration Below the Optimum
1. Perform full sanitization on the Pilot Line System.
2. Fill the $1^{st}$ flume tank, $2^{nd}$ flume tank, $1^{st}$ reservoir, $2^{nd}$ reservoir, $1^{st}$ filtering tank, and $2^{nd}$ filtering tank with tap water.
3. Recycle the water through the system until the water in the system is being cooled down to 40° F.
4. Switch on the by-passes for the $1^{st}$ and $2^{nd}$ flume tank systems so that water would not be going through the filtering systems but only recycling from the flume tank to its associate reservoir continuously.
5. Add the chemical ingredients to both tank until the target processing limit is reached
6. Verify the concentration of chlorinated water by the probe of the HACH System at the $1^{st}$ flume tank (F1), $1^{st}$ Reservoir (R1), $2^{nd}$ Flume tank (F2), and the $2^{nd}$ Reservoir (R2)
7. Collect water samples from F1 and F2.
8. Assemble the Romaine Lettuce Bins next to the dumpster.
9. Transfer Romaine Lettuce leaves from the bin to the conveyor.
10. Ensure that the lid above the F1 is closed. Turn the "ON/OFF" switch of the translicer to "ON".
11. Turn the conveyor for transferring leaves into the translicer to "ON".
12. Ensure that the chopped Romaine are delivered evenly into the flume tank without aggregation and clumping.
13. Collect three untreated bags of Romaine Lettuce from each bin (1 top, 1 middle, and 1 bottom).
14. Collect three treated bags of Romaine Lettuce at the end of F2 (1 beginning, 1 middle, and 1 end of the bin)
15. Verify the pH, temperature, and the concentration of chlorinated water at the $1^{st}$ flume tank (F1), $1^{st}$ Reservoir (R1), $2^{nd}$ · Flume tank (F2), and the $2^{nd}$ Reservoir (R2) before and after processing a bin.

16. Place white totes at the bottom of the locations with water spill. Return the spilt water back into the flume tank as needed.

17. Place white totes at the bottom outlets of the centrifuge to collect liquid that would be spin off from the leaves. Return the collected water back into the flume tank as needed.

18. Enumerate the microbial population (APC and Yeast and mold) on the collected samples.

Results and Conclusions

TABLE 5.1

Depletion of Peroxyacetic acid/PA with no Lactic acid/LA in the presence of organic matter based on commercial scale test.
Product: Diced Romaine Lettuce
Volume of sanitizer 600 gallons
Wash water Temp 38 to 40 F.

| Wt. of Diced Romaine added (lb) | Cumulative Wt. of Diced Romaine added (lb) | PA (ppm) | LA (ppm) | Peroxide (ppm) |
|---|---|---|---|---|
| 0.0 | 0.0 | 84.8 | 0 | 7.5 |
| 55.2 | 55.2 | 83.3 | 0 | 7.4 |
| 59.7 | 114.9 | 82.7 | 0 | 7.4 |
| 42.3 | 157.2 | 82.4 | 0 | 7.4 |
| 50.6 | 207.7 | 82.0 | 0 | 7.4 |
| 65.2 | 272.9 | 81.4 | 0 | 7.3 |
| 52.9 | 325.8 | 81.0 | 0 | 7.3 |
| 45.5 | 371.3 | 80.5 | 0 | 7.1 |
| 53.4 | 424.7 | 79.6 | 0 | 6.9 |
| 78.0 | 502.6 | 78.7 | 0 | 6.9 |
| 62.3 | 565.0 | 78.4 | 0 | 6.9 |
| 64.0 | 629.0 | 77.7 | 0 | 6.4 |
| 68.1 | 697.1 | 76.1 | 0 | 6.4 |
| 65.6 | 762.7 | 75.4 | 0 | 6.1 |
| 63.9 | 826.6 | 74.7 | 0 | 6.0 |
| 69.5 | 896.2 | 73.7 | 0 | 6.0 |
| 53.7 | 949.9 | 73.1 | 0 | 6.0 |

| | |
|---|---|
| Amount of PA consumed | 11.7 ppm |
| Pounds of PA consumed | 0.012078 lb |
| Pounds of Romaine treated | 949.90 lb |
| Depletion of PA | 0.000013 lb of PA per lb of Romaine |

TABLE 5.2

Reduction of indigenous microorganisms by peroxyacetic acid with no Lactic acid wash water based on commercial scale test.

| | Aerobic Plate Counts Log cfu/g |
|---|---|
| Untreated | 3.4 |
| PA Wash Water | 2.7 |
| Log Reduction | 0.7 |

TABLE 5.3

Depletion of test FE sanitizer wash water (Peroxyacetic acid/PA/PAA with Lactic acid/LA)) in the presence of organic matter based on commercial scale test.
Product: Diced Romaine Lettuce
Volume of sanitizer 600 gallons
Wash water Temp 38 to 40 F.

| Wt. of Diced Romaine added (lb) | Cumulative Wt. of Diced Romaine added (lb) | PA (ppm) | LA (ppm) | Peroxide (ppm) |
|---|---|---|---|---|
| 0.0 | 0.0 | 84.8 | 0 | 7.5 |
| 55.2 | 55.2 | 83.3 | 0 | 7.4 |
| 59.7 | 114.9 | 82.7 | 0 | 7.4 |
| 42.3 | 157.2 | 82.4 | 0 | 7.4 |
| 50.6 | 207.7 | 82.0 | 0 | 7.4 |
| 65.2 | 272.9 | 81.4 | 0 | 7.3 |
| 52.9 | 325.8 | 81.0 | 0 | 7.3 |
| 45.5 | 371.3 | 80.5 | 0 | 7.1 |
| 53.4 | 424.7 | 79.6 | 0 | 6.9 |
| 78.0 | 502.6 | 78.7 | 0 | 6.9 |
| 62.3 | 565.0 | 78.4 | 0 | 6.9 |
| 64.0 | 629.0 | 77.7 | 0 | 6.4 |
| 68.1 | 697.1 | 76.1 | 0 | 6.4 |
| 65.6 | 762.7 | 75.4 | 0 | 6.1 |
| 63.9 | 826.6 | 74.7 | 0 | 6.0 |
| 69.5 | 896.2 | 73.7 | 0 | 6.0 |
| 53.7 | 949.9 | 73.1 | 0 | 6.0 |

| | |
|---|---|
| Amount of PAA consumed | 10.7 ppm |
| Pounds of PAA consumed | 0.011 lb |
| Pounds of Romaine treated | 4011 lb |
| Depletion of PAA | 0.0000028 lb of PAA per lb of Romaine |

TABLE 5.4

Reduction of indigenous microorganisms by FE sanitizer wash water (Peroxyacetic acid with Lactic acid) based on commercial scale test.

| | Aerobic Plate Counts Log cfu/g |
|---|---|
| Untreated | 5.1 |
| FE Wash Water | 2.5 |
| Log Reduction | 2.6 |

TABLE 5.5

Depletion of 10 ppm chlorinated wash water in the presence of organic matter based on commercial scale test.
Product: Diced Romaine Lettuce
Volume of sanitizer 600 gallons
Wash water Temp 38 to 40 F.

| Wt. of Diced Romaine added (lb) | Cumulative Wt. of Diced Romaine added (lb) | pH | Free Chlorine ppm |
|---|---|---|---|
| 0 | 0.0 | 7.1 | 7.6 |
| 286.5 | 286.5 | 7.8 | 1.2 |

| | |
|---|---|
| Amount of free chlorine consumed | 6.4 ppm |
| Pounds of free chlorine consumed | 0.006594 lb |
| Pounds of Romaine treated | 287 lb |
| Depletion of free chlorine | 0.000023 lb of free chlorine per lb of Romaine |

TABLE 5.6

Reduction of indigenous microorganisms by chlorinated wash water based on commercial scale test.

| | Aerobic Plate Counts Log cfu/g |
|---|---|
| Untreated | 5.1 |
| Chlorinated Water | 3.9 |
| Log Reduction | 1.2 |

The depletion of peroxyacetic acid in the FE sanitizer was 5-fold (500%) less than that of the peroxyacetic acid solution with no addition lactic acid. This shows that under the same volume and concentration of peroxyacetic acid, the tested FE sanitizer could disinfect 5 times more produce than the peroxyacetic acid sanitizer with no lactic acid addition. In addition the lbs of free chlorine required to treat a pound of Romaine was 8.5 folds (850%) more than that of the tested FE sanitizer thus indicating that per pound of the tested FE sanitizer could disinfect 8.5 times more produce than per pound of chlorinated water.

The $\log_{10}$ reduction of indigenous microorganism on the Romaine leaf for 73-84 ppm peroxyacetic acid wash water, FE sanitizer wash water (59 to 69 ppm PA and 2,389 to 2,724 ppm LA), and 1.2 to 7.6 ppm free chlorine wash water was 0.7, 2.6, and 1.2-$\log_{10}$, respectively. Although the FE sanitizer in the study was below the optimum lower limit, its $\log_{10}$ reduction on indigenous microorganisms attached on the Romaine leaf was still 2.2 and 3.7 fold, respectively, higher than that of the chlorinated water and peroxyacectic acid wash water.

All publications, patents and patent applications cited herein, whether supra or infra, are hereby incorporated by reference in their entirety to the same extent as if each individual publication, patent or patent application was specifically and individually indicated to be incorporated by reference.

What is claimed is:

1. A method of reducing the amount of a microbial contaminant on the surface of a cut leafy vegetable comprising contacting the surface of the cut leafy vegetable with an aqueous solution comprising:
   i) peroxyacetic acid in a concentration from 50 to 100 ppm, and
   ii) L(+) lactic acid in a concentration from 0.1 to 0.6% (w/w), inclusive, wherein the aqueous solution has a pH from 2.5 to 4.5;
   wherein the contacting is for a period of time from 20 seconds to 2 minutes at a temperature between 35° F. and 45° F. and the amount of the microbial contaminant on the cut leafy vegetable is reduced.

2. The method of claim 1, wherein the concentration of the peroxyacetic acid in the solution is from 60 to 80 ppm, and the concentration of the lactic acid in the solution is from 0.1% to 0.4% (w/w).

3. The method of claim 1, wherein the solution is substantially free of nonionic surfactants, cationic surfactants or anionic surfactants.

4. The method of claim 1, wherein the aqueous solution is formed by combining a solution of the lactic acid which is substantially free of hydrogen peroxide with a solution of the peroxyacetic acid.

5. The method of claim 1, wherein the lactic acid and the peroxyacetic acid are provided as a concentrate and diluted with water to form the aqueous solution.

6. The method of claim 1, wherein the contacting sanitizes the cut leafy vegetable by killing or inhibiting the growth of bacteria on, or attached to, the cut leafy vegetable.

7. The method of claim 1, wherein the solution contains less than 300 ppm of an anionic surfactant.

8. The method of claim 1, wherein the cut leafy vegetable is a lettuce.

9. The method of claim 1, wherein the cut leafy vegetable is selected from the group consisting of spinach, cabbage, arugula, radicchio, escarole, kale, collard greens, bok choy, parsley, endive, mustard plant, chives, cilantro, and Napa cabbage.

10. The method of claim 1, wherein the cut vegetable is immersed in the solution and the solution is then removed by rinsing or centrifugation.

11. The method of claim 1, wherein the microbial contaminant is a bacterial human pathogen.

12. The method of claim 11, wherein the bacterial human pathogen is a strain of *E. coli* O157:H7, *Listeria monocytogenes*, or *Salmonella*.

13. The method of claim 1, wherein the microbial contaminant is an indigenous microorganism typically found on the surface of the cut leafy vegetable.

14. The method of claim 1, wherein the spoilage or decay of the cut produce is reduced.

15. The method of claim 1, wherein the aqueous solution is free of surfactant.

* * * * *